United States Patent [19]

Komurasaki et al.

[11] Patent Number: 5,783,417
[45] Date of Patent: Jul. 21, 1998

[54] HUMAN-DERIVED TUMOR CELL GROWTH INHIBITORS

[75] Inventors: Toshi Komurasaki; Kiyoshi Nakazawa; Hitoshi Toyoda; Masayoshi Takahashi; Daisuke Uchida; Kazunori Hanada, all of Tokyo; Shigezo Udaka, Aichi, all of Japan

[73] Assignee: Taisho Pharmaceutical Co., Ltd., Japan

[21] Appl. No.: 549,757

[22] PCT Filed: Jun. 2, 1994

[86] PCT No.: PCT/JP94/00895

§ 371 Date: Feb. 5, 1996

§ 102(e) Date: Feb. 5, 1996

[87] PCT Pub. No.: WO94/29340

PCT Pub. Date: Dec. 22, 1995

[30] Foreign Application Priority Data

Jun. 4, 1993 [JP] Japan ............................. 5-134854
Jun. 4, 1993 [JP] Japan ............................. 5-134855

[51] Int. Cl.⁶ ............................. C12N 15/12; C12N 15/74; C12N 15/75

[52] U.S. Cl. ................. 435/69.1; 435/69.5; 435/252.31; 435/320.1; 530/324; 536/23.5; 536/24.1

[58] Field of Search ............. 435/69.1, 69.5, 435/252.31, 320.1; 530/324; 536/23.5, 24.1

[56] References Cited

U.S. PATENT DOCUMENTS

| 4,524,145 | 6/1985 | Matson ............................. 514/43 |
| 5,384,394 | 1/1995 | Kamurasaki et al. ............. 530/324 |
| 5,523,391 | 6/1996 | Komurasaki ....................... 536/23.5 |

FOREIGN PATENT DOCUMENTS

| 4211698 | 8/1992 | Japan. |
| 9311233 | 6/1993 | WIPO. |

*Primary Examiner*—Stephen Walsh
*Assistant Examiner*—David S. Romeo
*Attorney, Agent, or Firm*—Lorusso & Loud

[57] ABSTRACT

A DNA fragment encoding a novel human-derived tumor cell growth inhibitor can be obtained from a cDNA library originating from human colon tumor cell, using as a DNA probe a DNA fragment encoding mouse human-derived tumor cell growth inhibitor. An expression plasmid bearing a promoter originating from *Bacillus brevis*, a signal peptide originating from *Bacillus* brevis and a DNA fragment encoding human-derived tumor cell growth inhibitor downstream of the signal peptide is constructed and *Bacillus brevis* is transformed by the expression plasmid. The resulting transformant is incubated to secret the novel inhibitor out of the cell so that the novel inhibitor can be produced efficiently.

7 Claims, 14 Drawing Sheets

FIG. 1

27                                                        54
GTG CAG ATT ACA AAG TGT AGT TCT AGT GAC ATG GAC GGC TAC TGC TTC CAT GGC CAG
Val Gln Ile Thr Lys Cys Ser Ser Ser Asp MET Asp Gly Tyr Cys Leu His Gly Gln 81                                                        108
TGC ATC TAC CTG GTG GAC ATG AGA GAG AAA TTC TGC AGA TGT GAA CTG GGC TAC
Cys Ile Tyr Leu Val Asp MET Arg Glu Lys Phe Cys Arg Cys Glu Val Gly Tyr

135
ACT GGT CTG CGA TGT GAG CAC TTC TTT CTA
Thr Gly Leu Arg Cys Glu His Phe Phe Leu

NUCLEOTIDE SEQUENCE (SEQ. I.D. NO. 5) OF THE DNA FRAGMENT ENCODING mTG-700 AND ITS AMINO ACID SEQUENCE (SEQ. I.D. NO. 6)

← 1200 BASE PAIRS

ANALYSIS OF HUMAN CHROMOSOMAL DNA FRAGMENT
BY SOUTHERN HYBRIDIZATION

FIG. 4

```
         11            20            29            38            47
)
TC ACA GCT TTA GTT CAG ACA GAA GAC AAT CCA CGT GTG GCT CAA GTG TCA ATA
   Thr Ala Leu Val Gln Thr Glu Asp Asn Pro Arg Val Ala Gln Val Ser Ile 56            65            74            83            92           101

ACA AAG TGT AGC TCT GAC ATG AAT GGC TAT TGT TTG CAT GGA CAG TGC ATC TAT
Thr Lys Cys Ser Ser Asp MET Asn Gly Tyr Cys Leu His Gly Gln Cys Ile Tyr 110           119           128           137           146           155

CTG GTG GAC ATG AGT CAA AAC TAC TGC AGG TGT GAA GTG GGT TAT ACT GGT GTC
Leu Val Asp MET Ser Gln Asn Tyr Cys Arg Cys Glu Val Gly Tyr Thr Gly Val 164           173           182           191           200           209

CGA TGT GAA CAC TTC TTT TTA ACC GTC CAC CAA CCT TTA AGC AAA GAG TAT GTC
Arg Cys Glu His Phe Phe Leu Thr Val His Gln Pro Leu Ser Lys Glu Tyr Val 218           227           236           245           254           263

GCT TTG ACC GTG ATT CTT ATT ATT TTG TTT CTT ATC ACA GTC GTC GGT TCC ACA
Ala Leu Thr Val Ile Leu Ile Ile Leu Phe Leu Ile Thr Val Val Gly Ser Thr 272           281           290           299           308           317

TAT TAT TTC TGC AGA TGG TAC AGA AAT CCA AAA AGT AAA GAA CCA AAG AAG GAA
Tyr Tyr Phe Cys Arg Trp Tyr Arg Asn Arg Lys Ser Lys Glu Pro Lys Lys Glu 326           335           344           353           362           378
                                                      )
TAT GAG AGA GTT ACC TCA GGG GAT CCA GAG TTG CCG CAA GTC TGA ATGGCGCCAT
Tyr Glu Arg Val Thr Ser Gly Asp Pro Glu Leu Pro Gln Val 388           398           408           418           428

CAAACTTATG GGCCAGGGAT AACAGTGTGC CTGGTTAATA TTAATATTCC ATTTT
```

NULEOTIDE SEQUENCE (SEQ. I.D. NO. 13) OF THE cDNA FRAGMENT OBTAINED FROM HCT-15 AND AMINO ACID SEQUENCE (SEQ. I.D. NO. 15) DEDUCED THEREFROM

FIG. 5

```
         10        20        30        40
VQITKCSSDMDGYCLHGQCIYLVDMREKFCRCEVGYTGLRCEHFFL    46    MOUSE (Seq.I.D. No.15)
| ||||||| |||||||||||||||    |||||||| |||||||
VSITKCSSDMNGYCLHGQCIYLVDMSQNYCRCEVGYTGVRCEHFFL    46    HUMAN (Seq.I.D. No.16)
         10        20        30        40
```

COMPARISON IN AMINO ACID SEQUENCE BETWEEN
HUMAN TG-700 AND MOUSE TG-700

FIG. 6

```
                                                                          54
27
GTG TCA ATA ACA AAG TGT AGC TCT GAC ATG AAT GGC TAT TGT TTG CAT GGA CAG
Val Ser Ile Thr Lys Cys Ser Ser Asp MET Asn Gly Tyr Cys Leu His Gly Gln 108
81
TGC ATC TAT CTG GTG GAC ATG AGT CAA AAC TAC TGC AGG TGT GAA GTG GGT TAT
Cys Ile Tyr Leu Val Asp MET Ser Gln Asn Tyr Cys Arg Cys Glu Val Gly Tyr

135
ACT GGT GTC CGA TGT GAA CAC TTC TTT TTA
Thr Gly Val Arg Cys Glu His Phe Phe Leu
```

NUCLEOTIDE SEQUENCE (SEQ. I.D. NO. 17) OF THE cDNA FRAGMENT ENCODING HUMAN TG-700 AND THE AMINO ACID SEQUENCE DEDUCED THEREFROM (SEQ. I.D. NO. 18)

FIG. 12 ELUTION PROFILE OF hTG-700 BY HPLC ON μ Bondshere C18

TUMOR CELL GROWTH INHIBITOR ACTIVITY OF hTG-700

DETECTION OF hTG-700 BY WESTERN BLOTTING

HUMAN-DERIVED TUMOR CELL GROWTH INHIBITORS

This application is a PCT/JP94/100895 filed Jun. 2, 1994.

BACKGROUND OF THE INVENTION

1. Technical Field

The present invention relates to a novel human-derived tumor cell growth inhibitor, a DNA fragment encoding the inhibitor, an expression plasmid of said human-derived tumor cell growth inhibitor bearing the DNA fragment, *Bacillus brevis* transformed by the expression plasmid, and a method for producing the human-derived tumor cell growth inhibitor using *Bacillus brevis* by a genetic engineering technique.

2. Background Art

Synthetic drugs such as chemotherapeutic agents or immunotherapeutic agents have been heretofore widely used as anti-tumor agents. However, these drugs generally encounter problems that their specificity is low and side-effects are serious. On the other hand, many tumor cell growth inhibitors have been found in tissue culture cells. These inhibitors could be such anti-tumor agents that would be highly specific and would have minimized side-effects. Representative examples of such inhibitors are interferon, lymphotoxin and tumor necrosis factor (TNF).

Recently, a tumor cell cytotoxic factor obtained from human fibroblast and a tumor cell growth inhibitor obtained from human lung cancer cells are reported in Japanese Patent KOKAI Nos. 1-148197 and 1-187094, respectively.

On the other hand, some cell growth inhibitors are isolated from the fibroblastic 3T3 cell line established from the cells obtained from Swiss fetal mice. For example, Natraj et al. has reported that a growth inhibitor was obtained from the cell membrane of 3T3 cells in the stationary phase, cf., Proc. Natl. Acad. Sci. U.S.A., 75, 6115–6119 (1978). Harel et al. has reported that a growth inhibitor having a molecular weight of 40 kDa was obtained from the culture supernatant of 3T3 cells, see J. Cell. Physiol., 119, 101–106 (1984), ibid., 123, 139–143 (1985). However, it is known that these growth inhibitors all fail to show any significant inhibitory action on tumor cells.

A mouse-derived tumor cell growth inhibitor isolated and purified from the culture supernatant of the established cell line NIH3T3-sf, which is obtained by focus cloning from NIH3T3 cells (J. Virol., 4, 549 (1969)), one of fibroblastic 3T3 cell lines established from Swiss fetal mice, is reported in Japanese Patent Application No. 3-11950 as the inhibitor having a significantly inhibitory activity on tumor cells. This mouse-derived tumor cell growth inhibitor exhibits a potent growth inhibition activity on tumor cells such as human promyelogenous leukemia cells or human cervical carcionoma cells and is expected to be effective as a new drug for the treatment of cancer. However, the inhibitor is a mouse-derived one so that there might be an antigenicity problem when applied to human.

DISCLOSURE OF THE INVENTION

The present inventors previously succeeded in cloning of cDNA encoding the mouse-derived tumor cell growth inhibitor which was isolated from the culture supernatant of NIH3T3-sf cells described above and already filed PCT/JP92/01580 directed to its nucleotide sequence.

In order to obtain a novel human-derived tumor cell growth inhibitor, the present inventors have made studies on cloning of cDNA encoding a human-derived tumor cell growth inhibitor from human placenta chromosomal DNA-derived DNA library and from human colon tumor cell-derived cDNA library and found a novel human-derived tumor cell growth inhibitor and a DNA fragment encoding the inhibitor.

The present inventors have made further studies to provide an industrially advantageous method for producing the inhibitor by recombinant DNA technique, using the DNA fragment encoding the human-derived tumor cell growth inhibitor. As a result, it has been discovered that by expressing the inhibitor using a promoter and a DNA fragment encoding a signal peptide as a regulator gene, derived from *Bacillus brevis* and using *Bacillus brevis* as a host, the inhibitor can be secreted out of the cell to produce the inhibitor in a large quantity. The present invention has thus been accomplished.

That is, an object of the present invention is to provide a human-derived tumor cell growth inhibitor having an amino acid sequence represented by formula (1):(Seq. I.D. No. 1)

Val — Ser — Ile — Thr — Lys — Cys — Ser — Ser —  (1)
Asp — Met — Asn — Gly — Tyr — Cys — Leu — His —
Gly — Gln — Cys — Ile — Tyr — Leu — Val — Asp —
Met — Ser — Gln — Asn — Tyr — Cys — Arg — Cys —
Glu — Val — Gly — Tyr — Thr — Gly — Val — Arg —
Cys — Glu — His — Phe — Phe — Leu

Another object of the present invention is to provide a DNA fragment encoding the human-derived tumor cell growth inhibitor having the amino acid sequence shown by formula (1).

A further object of the present invention is to provide a DNA sequence comprising a promotor derived from *Bacillus brevis*, a DNA fragment encoding a signal peptide derived from *Bacillus brevis*, and a DNA fragment coding for the human-derived tumor cell growth inhibitor having the amino acid sequence of formula (1) defined above.

A still further object of the present invention is to provide an expression plasmid for the human-derived tumor cell growth inhibitor comprising the DNA sequence described above.

A still further object of the present invention is to provide *Bacillus brevis* transformed by the expression plasmid.

A still further object of the present invention is to provide a method for preparing the human-derived tumor cell growth inhibitor which comprises culturing *Bacillus brevis* described above in a medium to express and extracellularly secrete the human-derived tumor cell growth inhibitor, and then recovering the human-derived tumor cell growth inhibitor from the medium.

BRIEF DESCRIPTION OF DRAWINGS

FIG. 1 shows a nucleotide sequence of the DNA fragment encoding mouse-derived tumor cell growth inhibitor and its amino acid sequence.

FIG. 4 indicates a nucleotide sequence of the cDNA fragment obtained from human colonel tumor cell HCT-15 and an amino acid sequence deduced therefrom.

FIG. 5 is a comparison in amino acid sequence between the human-derived tumor cell growth inhibitor.

FIG. 6 shows a nucleotide sequence of the cDNA fragment encoding the human-derived tumor cell growth inhibitor and an amino acid sequence deduced therefrom.

BEST MODE FOR CARRYING OUT THE INVENTION

Figure 2:
FIG. 2 shows an analysis pattern, i.e., an autoradiogram of human placenta chromosomal DNA fragment by Southern hybridization.

The human-derived tumor cell growth inhibitor (abbreviated as hTG-700 or human TG-700) of the present invention can be obtained by cloning a DNA fragment encoding the inhibitor, constructing an expression vector bearing the DNA fragment, inserting into a host cell for expression. Alternatively, the inhibitor can also be obtained by chemical synthesis based on the amino acid sequence deduced from the DNA fragment encoding hTG-700.

The DNA fragment encoding hTG-700 can be prepared by cloning from human cell-derived CDNA library using mouse-derived tumor cell growth inhibitor (hereinafter abbreviated as mTG-700 or mosue TG-700) having a known amino acid sequence.

mTG-700 is isolated from the culture supernatant of NIH3T3-sf, which is established cell line derived from 3T3 cell and its amino acid sequence is reported in Japanese Patent Application Laid-Open No. 4-211698 and EP 460910. The amino acid sequence of mTG-700 is shown in FIG. 1. Cloning of cDNA encoding the amino acid sequence can be performed in a conventional manner.

Firstly, mRNA is isolated and purified from NIH3T3-sf cells. cDNA complementary of mRNA is prepared and bound to lambda phage gt10. Phage particles are then formed by in vitro packaging (Hohn et al., Proc. Natl. Acad. Sci. U.S.A., 74, 3259 (1977)) to obtain cDNA library. Next, some oligonucleotides deduced from the amino acid sequence of mTG-700 are chemically synthesized. Using the oligonucleotides as primers and the cDNA library above as a template, various DNA fragments encoding mTG-700 are amplified by the PCR method (Saiki et al., Science, 230, 1350 (1985)). These nucleotide sequences are determined by the dideoxy chain terminator method (Sanger, F. et al., Proc. Natl. Acad. Sci. U.S.A., 74, 5463 (1977)). Based on the information and the amino acid sequence of mTG-700, the nucleotide sequence of DNA encoding mTG-700 can be determined. The thus determined nucleotide sequence of the DNA fragment encoding mTG-700 is shown in FIG. 1.

Using the DNA fragment encoding mTG-700 as a probe, cDNA encoding hTG-700 can be cloned from human-derived cDNA library, e.g., human placenta chromosomal DNA library or human colon tumor cell-derived cDNA library.

More specifically, the cloning of cDNA encoding hTG-700 can be performed by the following procedure.

First, DNA fragment encoding mTG-700 having the nucleotide sequence shown in FIG. 1 is labeled with, e.g., [$\alpha$-$^{32}$p] dCTP by multi-primed DNA labeling system (Amersham Co., Ltd.) to prepare DNA probe. Using the so prepared probe, human placenta chromosomal DNA (Clonetech Co., Ltd.) is digested with an appropriate restriction enzyme, e.g., HaeIII; DNA fragments obtained are subjected to Southern hybridization. DNA fragment considered to contain a gene highly homologous to the DNA fragment capable of hybridizing the probe and encoding mTG-700 can be detected by Southern hybridization and its molecular weight can be deduced. Then, DNA fragment around the deduced molecular weight is extracted from, e.g., agarose gel.

This DNA fragment is mixed with, e.g., lambda phage gt10-EcoRI arm to bind to each other, using T4 DNA ligase. A vector is thus constructed. Next, phage particles are formed by the in vitro packaging method to obtain human placenta chromosomal DNA fragment library.

Figure 3:
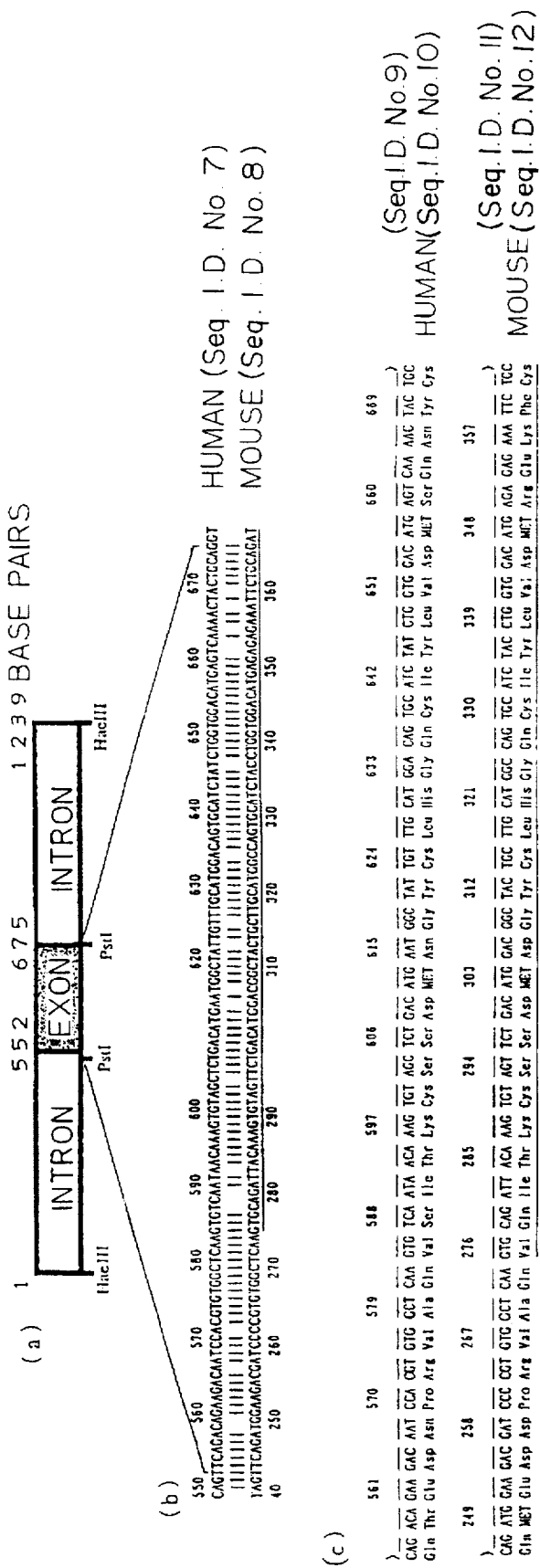
FIG. 3 (a) shows an outline of the chromosomal DNA fragment encoding a part of the human-derived tumor cell growth inhibitor; (b) is a comparison in nucleotide sequence between a part of the human-derived tumor cell growth inhibitor and a part of the cDNA fragment of a mouse-derived tumor cell growth inhibitor precursor; and (c) is a comparison in amino acid sequence between a part of the human-derived tumor cell growth inhibitor and a part of the cDNA fragment of the mouse-derived tumor cell growth inhibitor precursor.

With regard to the library, hybridization is performed using the same probe as described above, namely, the DNA fragment encoding mTG-700 labeled with [a-$^{32}$p] dCTP. The following screening gives a clone considered to bear a gene highly homologous to the DNA fragment encoding mTG-700. DNA is extracted from the clone and the nucleotide sequence of the DNA fragment extracted is determined by the dideoxy chain terminator method. FIG. 3 shows the nucleotide sequence of the DNA fragment thus determined. As is noted from FIG. 3, among the human placenta chromosomal DNA fragments obtained by digestion with restriction enzyme HaeIII, a DNA fragment having an amino acid showing high homology to mTG-700 is contained in the nucleotide sequence from 552 to 675 and is considered to be hTG-700.

Next, PstI fragment (520–674 nucleotide sequence in FIG. 3) in the human placenta chromosomal DNA fragment is labeled with [a-$^{32}$p] dCTP to prepare DNA probe. Using this DNA probe, cDNA is synthesized from MRNA of human colon tumor cell HCT-15 (Dainippon Pharmaceutical Co., Ltd., Cancer Research, 39, 1020 (1979)) and mixed with lambda phage gtlO-EcoRI arm. The cDNA library prepared by the in vitro packaging method is then subjected to screening.

A clone that can hybridize the DNA probe is obtained and DNA is extracted from the clone. The nucleotide sequence of DNA is determined by the dideoxy chain terminator method and compared with the nucleotide sequence of the DNA fragment encoding mTG-700. Thus, the nucleotide sequence of the desired DNA fragment encoding hTG-700 can be determined.

The nucleotide sequence of the DNA fragment encoding hTG-700 thus determined is shown by formula (2) ( Seq. I.D. No. 2) below:

brevis and the DNA fragment encoding the signal peptide as a regulator gene and using Bacillus brevis as a host to secrete a large quantity of hTG-700 out of the cell. It is thus possible to produce hTG-700 in a large quantity.

In these years, a keen attention has been increasingly brought to Bacillus brevis as a host used for recombinant DNA technique, since the bacteria hardly produces extra-cellular protease, see Udaka, Journal of Japan Agrichemical Association, 61 (6), 669–676 (1987). Typical examples of the promoter originating from Bacillus brevis include promoters for genes of major cell wall protein (MWP) of Bacillus brevis 47 (FERM P-7224) and Bacillus brevis H102 (FERM BP-1087). As the DNA fragment encoding the signal peptide derived from Bacillus brevis, there may be used a DNA fragment coding for the signal peptide of MWP gene from Bacillus brevis 47 or from Bacillus brevis H102. Such a signal peptide-coding DNA fragment is employed to secret hTG-700 out of the cell. In order to express hTG-700, SD sequence derived from Bacillus brevis at the 3' terminus of the promoter described above, initiation codon at the 3' terminus, the DNA fragment encoding the signal peptide described above and the DNA fragment encoding hTG-700 are connected in this order.

The promoter, the DNA fragment of SD sequence and the DNA fragment encoding the signal peptide are known and

```
                        27                                                             (2)
GTG TCA ATA ACA AAG TGT AGC TCT GAC ATG AAT GGC TAT TGT TTG CAT GGA CAG
                                81                                          108
TGC ATC TAT CTG GTG GAC ATG AGT CAA AAC TAC TGC AGG TGT GAA GTG GGT TAT
                                135
ACT GGT GTC CGA TGT GAA CAC TTC TTT TTA
```

The DNA fragment encoding hTG-700 having the nucleotide sequence of formula (2) determined as described above may also be chemically synthesized by known methods, e.g., by the triester phosphate method (Letsinger et al., J. Am. Chem. Soc., 91, 3350 (1969)).

Alternatively, the DNA fragment encoding hTG-700 may be prepared in a large quantity by synthesizing oligonucleotides corresponding to the 5'terminus and 3'terminus of the DNA fragment encoding hTG-700 using as a template the cDNA library prepared from mRNA of HCT-15 cells described above and amplifying the DNA fragment by PCR (Saiki et al., Science, 230, 1350 (1985)).

Based on the nucleotide sequence of the DNA fragment encoding hTG-700 thus cloned, the amino acid sequence of hTG-700 is determined and shown by formula (1) (Seq. I.D. No. 1) below:

Val — Ser — Ile — Thr — Lys — Cys — Ser — Ser — (1)
Asp — Met — Asn — Gly — Tyr — Cys — Leu — His —
Gly — Gln — Cys — Ile — Tyr — Leu — Val — Asp —
Met — Ser — Gln — Asn — Tyr — Cys — Arg — Cys —
Glu — Val — Gly — Tyr — Thr — Gly — Val — Arg —
Cys — Glu — His — Phe — Phe — Leu

The hTG-700 having the amino acid sequence of formula (1) can be chemically synthesized by, e.g., the solid phase method described in Merrifield, J. Am. Chem. Soc., 85, 2185 (1963)). In general, chemical synthesis based on the solid phase method may be carried out using a peptide automatic synthesizer, by following the standard operation program.

The hTG-700 of the present invention may also be prepared by recombinant DNA technique using the DNA fragment encoding hTG-700. That is, hTG-700 can be expressed using the promoter originating from Bacillus described in S. Udaka et al., Biotechnology and Genetic Engineering Reviews, 7, 113–146 (1989) and hence can be prepared by chemical synthesis through the phosphate triester method above. These fragments may also be prepared by cloning from, e.g., Bacillus brevis 47. These DNA fragments may be ligated to each other by utilizing an appropriate restriction enzyme site or via an appropriate linker. Alternatively, vectors such as pNU200 are known to bear the promoter, SD sequence and signal peptide-coding DNA fragment for the major cell wall protein gene from Bacillus brevis 47 (Udaka, Journal of Japan Agrichemical Association, 61 (6), 669–676 (1987) and Udaka et al., Proc. Natl. Acad. Sci. USA, 86, 3589–3593 (1989)) and accordingly, these vectors can be employed in its original form, without any modification.

More specifically, the expression vector can be constructed, e.g., by the following embodiment.

That is, the hTG-700 region is amplified by PCR, using as a template cDNA library containing cloned cDNA encoding hTG-700, to prepare MWP-hTG-700; MWP-hTG-700 is a DNA fragment bearing the hTG-700-coding DNA fragment and the DNA fragment with a part of the signal peptide-coding DNA sequence at the 5' terminus thereof and a termination codon at the 3' terminus, see FIG. 10.

Figure 9:
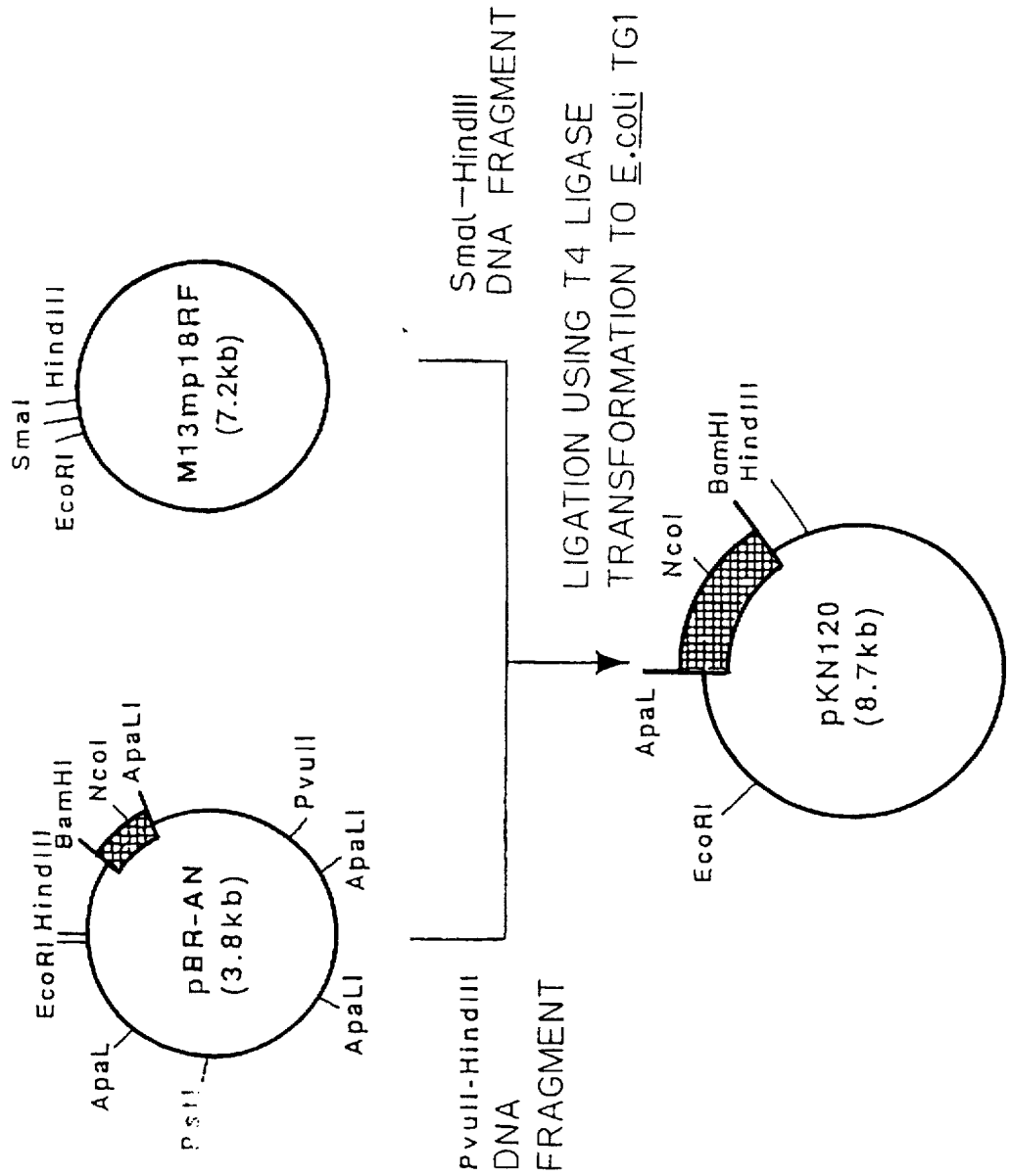
FIG. 9 indicates construction of plasmid pKN120 used as a cloning vector of the human-derived tumor cell growth inhibitor gene.

On the other hand, plasmid pKN120 having a part of the DNA sequence encoding the signal peptide and having the restriction enzyme NcoI site for ligation to the gene encoding hTG-700 is constructed as shown in FIG. 9.

Figure 11:
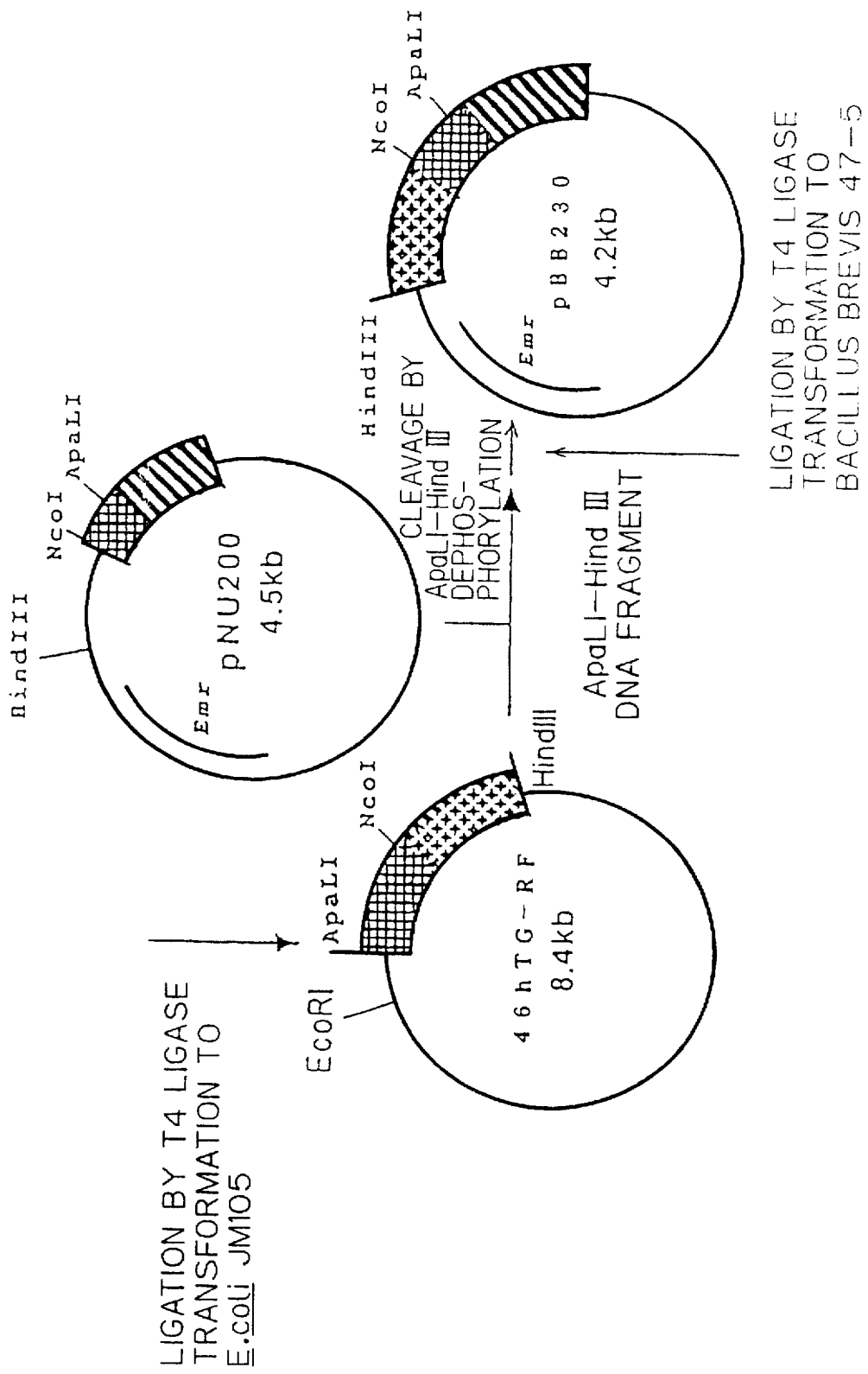
FIG. 11 shows construction of expression plasmid pBB230 of the human-derived tumor cell growth inhibitor.

Then MWP-hTG-700 is ligated to pKN120 by utilizing the restriction enzyme site NcoI to construct plasmid 46hTG-RF, see FIG. 11. This plasmid contains a part of the DNA sequence encoding the signal peptide and the hTG-700-coding DNA fragment and a termination codon subsequent thereto.

Next, ApaLl-HindIII DNA fragment containing MWP-hTG-700 is excised from the plasmid 46hTG-RF as shown in FIG. 11.

On the other hand, plasmid pNU200 is treated with restriction enzyme to obtain a DNA fragment bearing the promoter derived from *Bacilus brevis*, SD sequence and the DNA sequence encoding a part of the amino acid sequence in the N-terminal domain of the signal peptide. This DNA fragment is ligated to the MWP-hTG-700-bearing DNA fragment described above so that the desired expression plasmid pBB230 can be constructed, see FIG. 11.

In addition to the methods described above, the expression plasmid may also be constructed in a similar manner except for using, e.g., known plasmid pHY500. Plasmid pHY500 is known as a vector containing the DNA fragment encoding the promotor, SD sequence and signal peptide of the major cell wall protein gene from *Bacillus brevis* 47, see H. Yamagata et al., Proc. Natl. Acad. Sci. USA, 86, 3589–3593 (1989).

Representative examples of the host used to express hTG-700 are *Bacillus brevis* 47, *Bacillus brevis* 47-5 (FERM BP-1664) and mutants thereof.

A transformant can be obtained by inserting the expression plasmid into *Bacillus brevis* in a known manner (Takahashi et al., J. Bacteriol., 156, 1130 (1983).

The transformant is subjected to shake culture in an appropriate medium, e.g., $T_3$ modified medium (H. Yamagata et al., Proc. Natl. Acad. Sci. USA, 86, 3589–3593 (1989)) at a temperature of 15 to 42° C., preferably at 24 to 37° C., Continuous culture for 16 to 166 hours, preferably for 24 to 120 hours results in secretion of hTG-700 in the medium in such a form that the active steric structure is maintained.

The thus secreted hTG-700 can be purified from the medium in a conventional manner such as salting out, gel filtration chromatography, ion exchange chromatography, reversed phase chromatography, alone or in combination. The desired hTG-700 can thus be obtained. hTG-700 of the present invention may be in the form of pharmacologically acceptable salt. Examples of such salts are acid addition salts, e.g., hydrochloride, hydrobromide, hydroiodide, sulfate, acetate, citrate, succinate, fumarate, oxalate and p-toluenesulfonate; and base addition salts such as potassium, sodium, calcium, aluminum and ammonium salts.

hTG-700 of the present invention is effective for the treatment of leukemia, renal cancer and uterocervical cancer. Dosage of hTG-700 varies depending upon condition but a daily dose is generally in the range of 0.001 to 10 mg for adult. The dosage may be given once or divided into two to 4 times. hTG-700 is prepared into solid preparations such as tablets, pills, capsules or granules, or preparations such as injection, liquid, emulsion or suppositories. These preparations are prepared in a conventional manner; if necessary and desired, conventional additives such as aids, stabilizers, emulsifiers or diluents may also be added to the preparations.

Hereinafter the present invention will be described below in more detail, by referring to the examples and experiments.

EXAMPLE 1

Isolation of DNA fragment encoding hTG-700 and determination of its nucleotide sequence 1. Isolation of human chromosomal DNA fragment encoding a part of hTG-700

1) Analysis of human chromosomal DNA fragment by Southern hybridization

Southern hybridication of human chromosomal DNA fragment was carried out using as a probe cDNA fragment encoding mTG-700 having the nucleotide sequence shown in FIG. 1.

That is, 10 µg of human placenta chromosomal DNA (Clonetech Co., Ltd.) was digested with HaeIII (100 units) at 37° C. for 15 hours. The digestion produce was subjected to electrophoresis by 0.8% agarose gel and then transferred onto a nylon membrane (Hibond-N, Amersham Inc.) according to the method of Southern et al. (Southern, E.M., J. MO1. Biol., 98, 503 (1975). The DNA fragment was fixed by heat treatment at 80° C for 2 hours. The DNA fragment was fixed by heat treatment at 80° C. for 2 hours. The filter on which the obtained DNA fragment was immersed in a solution for hybridization (6×SSC, 5×Denhardt's solution, 0.5% SDS, 30% formamide, 100 µg/ml salmon sperm DNA fragment), followed by heating at 37° C. for 2 hours. Using multiprime DNA labeling system (Amersham Inc.), cDNA fragment encoding mTG-700 having the nucleotide sequence shown in FIG. 1 was labeled with $[\alpha^{32}p]$ dCTP and used as a probe. The probe was added to the solution for hybridization described above and the reaction was continued at 37° C. for 16 hours. After the reaction was completed, the filter was rinsed at room temperature with 1×SSC buffer containing 0.1% SDS. After washing at 37° C. for further 30 minutes with 0.1×SSC buffer containing 0.1% SDS, the filter was air-dried. The filter was brought into close contact with X ray film X-OMART AR (Eastman Kodak) and exposed to light at −80° C. for 16 hours. As the result, a band was observed at about 1200 base pairs, suggesting that human gene considered to code for human-derived tumor cell growth inhibitor would be present, see FIG. 2.

2) Construction of human chromosomal DNA fragment (1) Extraction of human chromosomal DNA fragment After 10 µg of human placenta chromosomal DNA (Clonetech) was digested with 100 units of HaeIII in the manner described in 1) above, electrophoresis was performed one 0.8% agarose gel and the DNA fragment at about 1200 base pairs was extracted as follows.

a. The DNA fragment at about 1200 base pairs was adsorbed onto DE81 Paper (Whatman) (Dretzen, G. et al., Anal. Biochem., 112, 295, 1981).

b. The paper was immersed in 300 µl of an eluent (1.5 M NaCl, 1 mM EDTA, 10 mM Tris-HCL, pH 8.00.

c. A mixture of phenol and chloroform (1:1) was added in an amount of 300 µl.

d. Agitation was followed by centrifugation at 10,000×g for 10 minutes.

e. The supernatant was withdrawn and 750 µl of ethanol was added to the residue.

f. The mixture was allowed to stand at −70° C. for an hour.

g. The system was centrifuged at 10,000×g for 10 minutes.

h. After dissolving in 10 µl of TE buffer (1 mM EDTA, 10 mM Tris-HCl, pH 8.00), a solution containing the DNA fragment at about 1200 base pairs was obtained.

(2) Ligation of human chromosomal DNA fragment to vector

The DNA fragment obtained in (1) above was mixed with lambda phage gtl0-EcoRI arm (manufactured by Strategene Co., Ltd.) and the two were ligated to each other using T4 DNA ligase.

(3) In vitro packaging

Phage particles were produced from the vector-ligated DNA fragment using in vitro packaging kit (Amersham) to construct the human chromosomal DNA library.

3) Screening of the human chromosomal DNA fragment library

About $6 \times 10^5$ of the recombinant phages obtained in 2)(3) described above were infected to 4 ml of *E. coli* NM514 which had been incubated overnight at 37° C. in LB medium (trypton: 10 g, yeast extract: 5 g, sodium chloride: 10 g/L). The seed medium was then inoculated in 20 LB medium plates of 9×14 cm each, containing 1.5% agar. Each of the LB medium plates was overlaid by 3 ml of LB medium containing 0.75% agarose and kept at 45° C. After incubation at 37° C. for 12 hours, a nylon membrane filter (HIBOND-N; Amersham) was brought in close contact for a minute with the plate in which plaques were formed. The filter was immersed in an alkali solution (1.5 M NaCl, 0.5 N NaOH) for 2 minutes and then in a neutral solution (3.0 M NaCl, 0.5 N Tris-HCl pH 7.0) for 5 minutes. After rinsing with 2×SSC, the filter was air-dried. The resulting filter was treated in the same manner as in 1—1) described above to fix the DNA fragment. Hybridization was carried out using as a probe the DNA fragment encoding mTG-700 labeled with [$\alpha$-$^{32}$p] dCTP, which was followed by exposure to light on a film. The area corresponding to the sensitized signal on the film was collected and immersed in TM buffer (10 mM Tris-HCl (pH 8.0), 10 mM MgSO$_4$) to extract the recombinant phages.

With respect to the thus obtained recombinant phages, screening was repeated in quite the same manner as described above to obtain 9 single plaques (positive clones) expected to contain the DNA fragment considered to code for the human-derived tumor cell growth inhibitor.

4) Analysis of nucleotide sequence

From the plaques prepared in 3) described above, DNA was extracted in a conventional manner and its nucleotide sequence was determined by the dideoxy chain terminator method (Sanger, F. et al., Proc. Natl. Acad. Sci. U.S.A., 74, 5463 (1977)), using 7-Deaza-Sequencing Kit (Toyobo Co., Ltd.). Homology of the nucleotide sequence to the mTG-700 cDNA fragment was examined. The results are shown in FIG. 3. As is noted from FIG. 3, comparison reveals that the region similar to a part of the CDNA fragment of mTG-700 precursor was observed from 550 to 675 bases in the nucleotide sequence, cf. FIG. 3 (b) in which the underlined portion indicates a part of the mature mTG-700 cDNA fragment. The region was translated into amino acids, which were similar to a part of the mTG-700 precursor, see FIG. 3 (c). According to the Cech's rule (Cech, T.D., Cell, 34, 713, 1983), it is assumed that the 552–675 region would be a translation site (exon) into a protein, see FIG. 3 (a).

Based on the foregoing results, it is considered that a part of the DNA fragment encoding hTG-700 would be contained in the chromosomal DNA fragment obtained from the plaques prepared in 3) above.

2. Isolation of the cDNA fragment encoding a full-length hTG-700 and determination of nucleotide sequence 1) Construction of cDNA library of HCT-15 cells (1) Extraction of mRNA from HCT-15 cells Human colonel tumor cells HCT-15 (Dainippon Pharmaceutical Co., Ltd., Cancer Research, 39, 1020, 1979) were cultured at 37° C. in 10% calf fetal serum-containing F medium in 5% $CO_2$. At the time when the cells reached confluence, the medium was removed. After washing once with PBS (−), PBS (−) was supplemented. The cells were then scraped out with a cell scraper and collected in a conical tube. After centrifugation at 1500×g for 5 minutes at room temperature, PBS (−) was added to suspend the cells therein. The suspension was again centrifuged to obtain the precipitates. From the precipitates, MRNA was extracted using mRNA Extraction Kit (manufactured by Pharmacia). Following this procedure, 58.3 µg of mRNA was purified from 2×108 cells.

(2) Synthesis of cDNA

Using the mRNA prepared in (1) as a template, cDNA was synthesized using oligo dT as a primer, by the use of cDNA Synthesis Kit (manufactured by Pharmacia). Following this procedure, 1.0 µg of cDNA was synthesized from 1.9 µg of mRNA.

(4) Ligation of cDNA to vector and in vitro packaging

The cDNA fragment synthesized as described in (2) above was ligated to EcoRI adapter by the procedure described in 1-2)-(2). The in vitro packaging was performed as in the procedure described in 1-2)-(3) to construct cDNA library.

2) Screening of cDNA library of HCT-15 cells The PstI fragment (520 to 674 base pairs; see FIG. 3) of the DNA fragment considered to encode a part of hTG-700 obtained in 1-3) described above was labeled with [$\alpha$-32p] dCTP using multi-prime DNA labeling system (Amersham Inc.) to prepare a DNA probe.

Using the DNA probe, screening of the CDNA library for HCT-15 cells obtained in 1)-(3) described above was performed. The screening proceeded as in the procedure described in 1-3) above. One positive clone considered to contain the DNA fragment encoding hTG-700 was obtained from about $6 \times 10^5$ recombinant phages.

3) Analysis of nucleotide sequence

From the clone obtained in 2) described above, the DNA fragment was extracted and its nucleotide sequence was determined by the method described in 1-4) above. FIG. 4 shows a part of the nucleotide sequence and the amino acid sequence deduced therefrom. Comparison was made between the amino acid sequence of hTG-700 expected from the DNA fragment and that of mTG-700, see FIG. 5. As is noted from FIG. 5, comparison reveals high homology in amino acid sequence of hTG-700 to mTG-700. Based on the structure of the N and C termini of mTG-700, it was assumed that hTG-700 would have Val at the N terminus and Leu at the C terminus (FIG. 4, the underlined portion) and have the amino acid sequence shown in FIG. 6. It was also assumed that the DNA fragment encoding hTG-700 would have the nucleotide sequence shown in FIG. 6.

EXAMPLE 2

Chemical synthesis of hTG-700

The peptide deduced from the amino acid sequence encoded by the nucleotide sequence shown in FIG. 6 was chemically synthesized by the 9-fluorenyl-methoxycarbonyl (Fmoc) method.

The Fmoc method (E. Atherton, C. J. Logan and R. C. Sheppard, J. Chem. Soc., Perkin Trans. 1, 1981, 538–546) is a very simple peptide synthesis for preparing a linear peptide which comprises repeating a series of operations for selective removal of α-amino-protecting Fmoc group from the carboxyl terminus of the desired peptide using a secondary amine and condensation of an amino acid with protected functional groups on the side chain, cutting the thus obtained peptide chain out of the solid phase resin and removing the protective groups on the side chain.

Then, the hTG-700 was synthesized in a 0.1 mmol scale using a peptide automatic synthesizer (Pepsyn 9050 Peptide Synthesizer: Millipore). Isolation from the solid phase resin with a half amount of the resin after the synthesis followed by removal of the protective groups on the side chain gave the linear peptide. Since hTG-700 was considered to have 3 pairs of S-S bond in the molecule thereof, only the side chain of cysteine was protected with such a protective group that was not split off by a conventional method for removal of protective groups. The thus obtained linear peptide was purified by chemoselective one-step purification (S. Funakoshi, H. Fukuda and N. Fujii, Proc. Natl. Acad. USA, 88, 6981–6985, 1991) and the protective group for cysteine on the side chain was then removed. Subsequently, air oxidation was performed to form intramolecular S-S bond. The peptide was purified by high performance liquid chromatography until a single product was obtained. The purified product was analyzed by Protein Sequencer Model 473A (Applied Biosystems); as the result, it was confirmed that the peptide had the amino acid sequence shown in FIG. 6. In the thus obtained hTG-700, the S—S bond was formed in the cysteine residues between 6 and 19, 14 and 30, and 32 and 41.

Experiment 1
Major cell growth inhibitory activity of hTG-700

With respect to hTG-700 obtained by chemical synthesis in Example 2, the activity was examined by the following evaluation system.

(1) Growth inhibitory activity on human uterocervical carcinoma HeLa

HeLa cells were inoculated on a 48-well plate (SUMILON) in $2 \times 10^4/250$ µl/10% FBS +DF/well followed by incubation for 24 hours. After the medium was removed, 250 µl of hTG-700-containing DF medium supplemented with 0.01% BSA was added to the system followed by incubation for 6 days. After the incubation, the cells were stripped out with 0.25% trypsin/0.002% EDTA and counted with Coulter Counter (Coulter). The growth inhibitory activity on HeLa cells is shown in terms of % when the activity in the intact group was made 100%.

The results are shown in Table 1.

TABLE 1

| | Growth inhibitory activity on human uterocervical carcinoma HeLa | |
|---|---|---|
| | Cell Count | (%) of Control |
| Control | $2.61 \times 10^5$ | 100 |
| Treated group | $0.47 \times 10^5$ | 18 |

(2) Growth inhibitory activity on various tumor cells
Tumor cells of HeLa (human uterus cancer), HCT-15 (human colonel tumor), T-13 (human renal tumor) and T-28 (human renal tumor) were inoculated, respectively, on a 48-well plate (SUMILON) in $5 \times 10^3/250$ µl /10% FBS +DF/well followed by incubation for 24 hours. After the medium was removed, 200 µl of hTG-700-containing DF medium supplemented with 0.1% BSA was added to the system followed by incubation for 6 days. The medium was removed. After washing with PBS (−), the cells were stripped out with 0.25% trypsin and counted with Coulter Counter (Coulter). The growth inhibitory activity was determined according to the following equation:

$$(\%) \text{ of Control} = \frac{\text{Cell count in the group treated with hTG-700}}{\text{Cell count in the intact group}} \times 100$$

TABLE 2

| | Growth inhibitory activity on tumor cells hTG-700 (µg/ml) | | | |
|---|---|---|---|---|
| Cell | 10 | 2 | 0.4 | 0.08 |
| HeLa | 12 | 47 | 64 | 96 |
| HCT-15 | 7 | 25 | 38 | 50 |
| T-13 | 2 | 8 | 19 | 56 |
| T-28 | 4 | 26 | 42 | 75 |

As is clearly seen from the results of Tables 1 and 2, novel hTG-700 provided by the present invention exhibits a tumor cell growth inhibitory activity and is thus expected to be a novel therapeutic agent for the treatment of tumors.

EXAMPLE 3

Production of hTG-700 by recombinant DNA technology

1. Cloning of DNA fragment encoding hTG-700
(1) Synthesis of oligonucleotides for amplification of hTG-700 gene by PCR Based on the nucleotide sequence of cDNA of hTG-700, oligonucleotides used as the primers at the 5′ terminus and 3′ terminus were prepared, respectively.

Figure 7:
FIG. 7 shows oligonucleotides used as primers for amplifying the DNA fragment by PCR.

That is, as shown in FIG. 7, synthetic oligonucleotide BB-15 containing NcoI linker, a part of the C-terminal coding region of the signal peptide for MWP (major cell wall protein) gene from *Bacillus brevis* 47 and the region encoding the amino acid in the N-terminal domain of hTG-700 was synthesized as the 5′ primer. As the 3′ primer, synthetic oligonucleotide BB-22 was designed and synthesized to have a nucleotide sequence complementary to the DNA sequence containing the C-terminal amino acid-coding region of hTG-700, a termination codon and HindIII linker. These oligo-nucleotides were prepared by DNA Synthesizer (ABI Inc., Model 380B) and purified by OPC Column (ABI Inc.).

(2) Amplification of hTG-700 gene by PCR and purification

And 58 Al of sterilized water to 10 µl of XgtlO library obtained in Example 1, 2-1)-(3) by cloning cDNA of HCT-15 cells;

Heat the mixture at 95° C. for 10 minutes;
Quench the mixture in ice water;
Add 100 pmols of BB-15, 100 pmols of BB-22,10 µl of x 10 buffer and finally 16 µl of 1.25 mM dNTP;

Add sterilized water to make the whole volume 100 μl; and,

Add 1 μl of Taq polymerase. Gene amplification by PCR:

Heat at 94° C. for a minute, at 40° C. for 2 minutes and at 72° C. for 3 minutes (repeat this cycle 30 times);

Add 10 μl of 3 M sodium acetate (pH 6.0) and 250 μl of ethanol;

Incubate at −70° C. for an hour;

Centrifuge at 10,000×g for 20 minutes;

Precipitate;

Add 300 pl of 70% ethanol;

Centrifuge at 10,000×g for 20 minutes;

Precipitate;

Dry the precipitates by a centrifugal evaporator;

Dissolve in 20 gl of TE buffer;

Add 5 μl of NcoI (12 units/gl), 4 μl of ×10 M buffer (100 mM Tris-HCl (pH 7.5), 100 mM $MgCl_2$, 10 mM dithiothreitol, 500 niM NaCl);

Add 11 μl of sterilized water;

Heat at 37° C. for 3 hours;

Heat at 65° C. for 10 minutes for inactivation;

Add 5 μl of HindIII (12 units/μl), 5 μl of ×10 K buffer (200 mM Tris-HCl (pH 8.5), 100 mM $MgCl_{21}$, 10 mM dithiothreitol, 1 M KCl );

Heat at 37° C. for 3 hours;

Subject to electrophoresis, 3% NuSieve: agarose (FMC Inc.) =3:1;

Adsorb the amplified DNA fragment onto DE81 Paper (Whatman);

300 μof eluent (1.5 M NaCl, 1 mM EDTA, 10 mM Tris-HCl (pH 8.0))

300 μof phenol:chloroform (1:1)

Agitate the mixture and then centrifuge the same at 10,000×g for 10 minutes;

And 750 μof ethanol to the supernatant;

Incubate at −70° C. for an hour;

Centrifuge at 10,000×g for 10 minutes; and,

Dissolve the precipitates in 12 μl of TE buffer (1 mM EDTA, 10 mM Tris-HCl (pH 8.0)).

Figure 10:
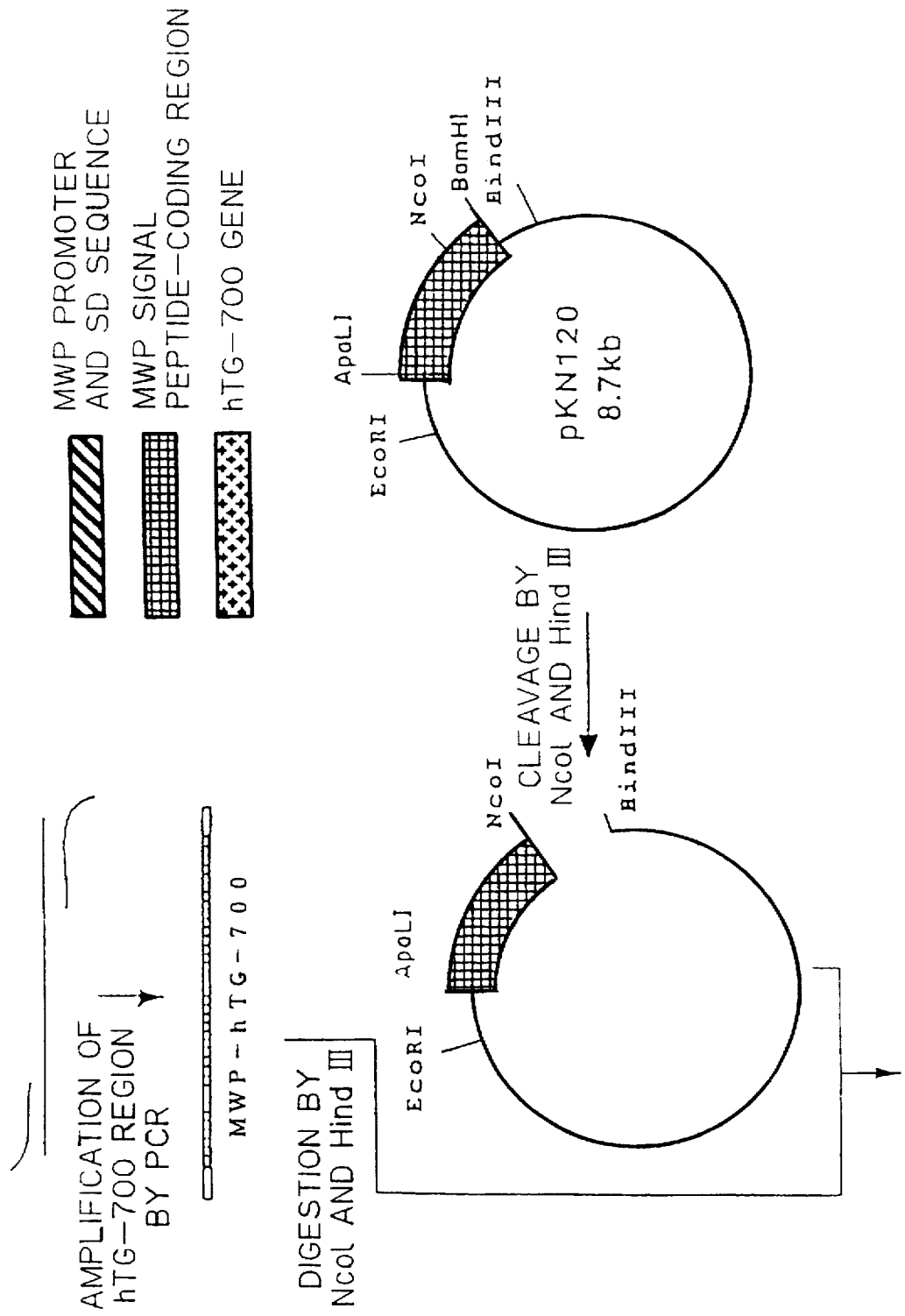
FIG. 10 shows digestion of plasmid pKN120 and the human-derived tumor cell growth inhibitor gene.

By performing the procedures above, MWP-hTG-700 DNA fragment is obtained, see FIG. 10.

2. Integration of hTG-700 gene in expression plasmid
(1) Construction of pBR-AN

Figure 8:
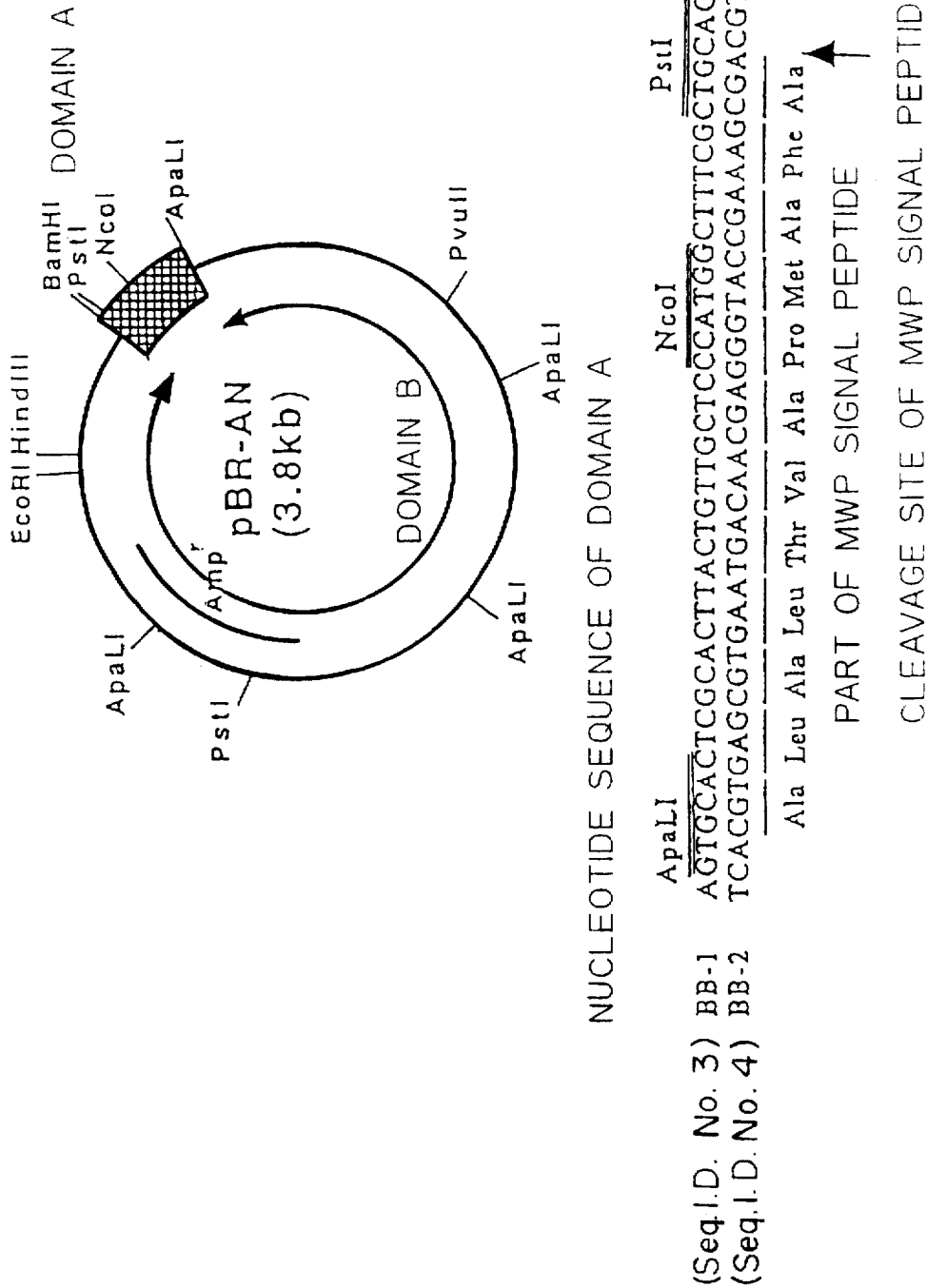
FIG. 8 shows the structure of plasmid PBR-AN bearing NcoI site and a DNA sequence encoding a part of the C-terminal region of the signal peptide of MWP which is one of the major cell wall proteins of *Bacillus brevis* 47.

In order to construct pKN120 later described, plasmid pBR-AN having NcoI site, which will be used for transduction of MWP-hTG-700 bearing a NcoI linker was constructed. As shown in FIG. 8, PBR-AN was constructed by ligating the following two DNAs. Domain A: Two synthetic oligonucleotides BB-1 and Bb-2 were synthesized. After purifying on OPC column, annealing was performed.

Domain B: BamHI-NruI fragment from *E. coli* plasmid pBR322 (Sutchliffe, J. G., Cold Spring Harbor Symposium, 43, 77–90, 1979)

(2) Digestion of M13mp18RFDNA by SmaI-HindIII and dephosphorylation

After 2 μg of M13mpl8RFDNA (Takara Shuzo) was digested by 24 units each of SmaI and HindIII at 37° C. for 3 hours, the digestion product was then dephosphorylated with calf intestinal phosphatase (Takara Shuzo). The product was dissolved in TE buffer in a final concentration of 0.1 μg/μl to obtain SmaI-HindIII DNA fragment of M13mpl8RF, see FIG. 9.

(3) Preparation of cloning vector pKN120

Ten micrograms of plasmid pBR-AN bearing a DNA sequence encoding the NcoI site and a part of the C-terminal region of the signal peptide for MAP (hereinafter referred to as NcoI-MWP region) was digested by 100 units of HindIII and 100 units of PvuII at 37° C. for 2 hours. The reaction product was electrophoresed on 3% NuSieve:agarose (3:1). Then the HindIII-ApaLl fragment containing the NcoI-MWP region was isolated and purified using DE81 paper and finally dissolved in 12 μl of TE buffer.

The resulting DNA solution (5 μl) was mixed with 2 μl of the SmaI-HindIII DNA fragment prepared in (2) above to effect ligation using T4 DNA ligase (Takara Shuzo). The reaction solution was transduced into *E. coli* JM105 (C. Yanisch-Perron, J. Vieira and J. Messing, Gene 33, 103–119, 1985) by the calcium method (Messing, J., Methods in Enzymology, 101, 20–78, 1983) to form plaques using JM105 as an indicator. The plaques were adsorbed to JM105 and incubated. From the cells RF-DNA was prepared by the alkali method (Birnboim, H. C. and Doly, J., Nucleic Acids Res., 7, 1513–1523, 1929). The desired plasmid, pKN120, bearing the HindIII-ApaLI DNA fragment containing the NcoI-MWP region was thus obtained, see FIG. 9.

(4) Cloninq of hTG-700 gene to pKN120

After 2 μg of pKN120 was digested by NcoI-HindIII, the digestion product was dephosphorylated with calf intestinal phosphatase (Takara Shuzo). The product was dissolved in TE buffer in a final concentration of 0.1 μg/pl, see FIG. 10. The resulting DNA solution (2 μl) was mixed with 5 μl of a DNA solution of MWP-hTG-700 containing hTG-700 amplified in 1-(2) above to effect ligation using T4 DNA ligase. The reaction solution was transformed to *E. coli* JM105 by the calcium method. RFDNA was prepared from the transformant according to the alkali method to obtain plasmid 46hTG-RF in which the hTG-700 gene was ligated downstream of the MWP signal peptide-coding region, see FIG. 11.

(5) Construction of expression plasmid PBB230

1) After 5 μg of pNU200 was digested by 50 units of ApaLI and 50 units of HindIII at 37° C. for 3 hours, the Domain A contains the NcoI site and the DNA fragment deleted of MWP signal peptide-encoding 5' terminal region.

digestion product was dephosphorylated by calf intestinal phosphatase. After electrophoresis on agarose gel, vector BB-1 (Seq. I.D. No. 3);
5'-AGTGCACTCGCACTTACTGTTGCTCCCATGGCTTTCGCTGCAG-3'

BB-2 (Seq I.D. No. 4);
5'-GATCCTGCAGCGAAAGCCATGGGAGCAACAGTAAGTGCGAGTGCACT-3'

DNA containing the promoter of MWP and SD sequence, the 5' terminal region of the DNA nucleotide sequence encoding signal peptide and erythromycin-resistant gene was purified using DE81 paper. The purified vector DNA was dissolved in 30 μl of TE buffer.

2) After 20 pg of 46hTG-RF was digested by 50 units each of restriction enzymes ApaLI and HindIII at 37° C. for 3 hours, the digestion product was subjected to electrophoresis on agarose gel. Thereafter, the ApaLI-HindIII DNA fragment was isolated and purified using DE81 paper to obtain the DNA fragment ligated with hTG-700 gene downstream of the DNA sequence encoding the 5' terminus-deleted MWP signal peptide, see FIG. 11. The DNA fragment was dissolved in 12 μl of TE buffer.

3) Ligation was performed between 2 μl of the dephosphorylated vector prepared in 1) above and 5 μl of the inserted DNA fragment containing hTG-700 gene, using T4 DNA ligase. These reaction solutions were transformed to *Bacillus brevis* 47-5 (H. Yamagata et al., J. Bacteriol., 169, 1239–1245, 1987) by the method of Takahashi et al., J. Bacteriol., 156, 1130–1134, 1983). Plasmid DNA was prepared from the transformant by the alkali method. Thus, pBB230 which was an expression plasmid of the desired hTG-700 and ligated to MWP promoter, SD sequence and hTG-700 gene downstream of the signal peptide-coding region, see FIG. 11.

3. Production of hTG-700 in Bacillus brevis

*Bacillus brevis* bearing pBB230 (pBB230/47-5) prepared in 2-(5) above was shake-cultured at 30° C. for 3 days in an appropriate medium, for example, $T_3$ modified medium (5 mM $MgCl_2$, 20 g Polypeptone P1 (Nippon Pharmaceutical Co., Ltd.), 6.5 g yeast extract (Nippon Pharmaceutical Co., Ltd.), 30 g glucose, 0.1 g uracil, per litter, adjusted pH to 7.0 with NaOH) supplemented with 10 μg/ml of erythromycin. Thereafter 20 g/l of glucose was added thereto followed by shake culture for further 2 days.

4. Assay for biological activity of hTG-700 produced by Bacillus brevis

For the purpose of assaying for biological activity, the culture supernatant was centrifuged and sterilized through ULTRAFREE C3 HV STRL (Millipore). The biological activity of hTG-700 in the supernatant was determined by growth stimulation activity on mouse Balb3T3 cells.

Mouse fibroblast-derived Balb3T3 was inoculated on 5% calf serum-containing Dulbecco's modified Eagle's medium charged in a 96-well plate in an amount of $1 \times 10^4/100$ μl medium/well. Incubation was performed at 37° C. for 48 hours under 5% $CO_2$ conditions. The culture broth was then changed by 0.5% calf serum-containing Dulbecco's modified Eagle's medium (0.5% CS-DME), followed by incubation for further 24 hours. The medium was then changed with 0.5% CS-DME containing 0.1 μg/ml to 100 ng/ml of authentic hTG-700 or a sample, followed by incubation at 37°C. for 20 hours. Labeling was effected for 4 hours by adding 0.25 μCi/well of [$^3$H] thymidine (Amersham) and [$^3$H] thymidine intake activity was quantitatively determined by β-plate system (Amersham). As the result, about 4 mg of hTG-700 was produced per liter of the medium.

5. Purification of hTG-700 produced by Bacillus brevis (1) O-Sepharose-C4. resin column After 100 liters of the culture supernatant of pBB230/47-5 incubated in the manner shown in 3. above was separated with S type ultra centrifuging machine (8,000 rpm, Kokusan Seiko), the supernatant was collected and filtered through Peristaltic Pump Cassette System (ultrafiltering membrane system, 0.3 μm filter, Fuji Filter). The filtrate was treated with 1 M Tris-HCl (pH 7.5) to adjust pH to 7.5 and was added to Q-Sepharose-$C_4$ resin column, which has been previously equilibrated with 5% acetonitrile.

| Column: | Q Sepharose FF (Pharmacia) |
| --- | --- |
| | φ16 cm × 10 cm |
| | $C_4$ resin (Chemco), φ16 cm × 15 cm |
| Flow rate: | 40 ml/min | hTG-700 is non-adsorptive to Q Sepharose but adsorbed to $C_4$ resin. After adsorption, the $C_4$ column was washed with 5% acetonitrile and eluted with 50% acetonitrile and 0.1% TFA solution (flow rate: 40 ml/min).

(2) S-Sepharose

Acetonitrile was removed from the active fraction obtained in (1) above, using an evaporator and 1 M acetate buffer (pH 4.0, sodium acetate-acetic acid) was then added to adjust the pH of the sample to 4. The sample was adsorbed to S-Sepharose column which had been equilibrated with 20 mYM acetate buffer and 5% acetonitrile. Elution was stepwise performed with eluent A and eluent B.

| Column: | S-Sepharose FF (Pharmacia) |
| --- | --- |
| | φ10 cm × 10 cm |
| Eluent A: | 20 mM acetate buffer (pH 4.0), 5% acetonitrile + 0.05 M NaCl |
| Eluent B: | 20 mM acetate buffer (pH 4.0), 5% acetonitrile + 0.5 M NaCl |
| Flow rate: | 50 ml/min |

(3) $C_4$ HPLC

The active fraction was obtained from those eluted with eluent B and purified by $C_4$ reverse phase HPLC.

| Column: | $C_4$, φ2.2 cm × 25 cm (Vydac) |
| --- | --- |
| Eluent A: | 10% acetonitrile, 0.1% TFA |
| Eluent B: | 40% acetonitrile, 0.1% TFA |
| Flow rate: | 15 ml/min |
| Fractionation: | 2 min |
| Gradient: | A → B (150 min) |

(4) $C_{18}$ HPLC

After an equal volume of 0.1% TFA solution was added to the active fraction (3) above, separation and purification were performed through $C_{18}$ column.

| Column: | μBondsphere $C_{18}$ (φ39 cm × 150 mm, Waters) |
| --- | --- |
| Eluent A: | 0.1% TFA |
| Eluent B: | 20% acetonitrile, 0.1% TFA |
| Eluent C: | 40% acetonitrile, 0.1% TFA |
| Flow rate: | 8 ml/min |
| Conditions: | A → B (5 mins) → B (5 mins) → C (120 mins) |

Figure 12:
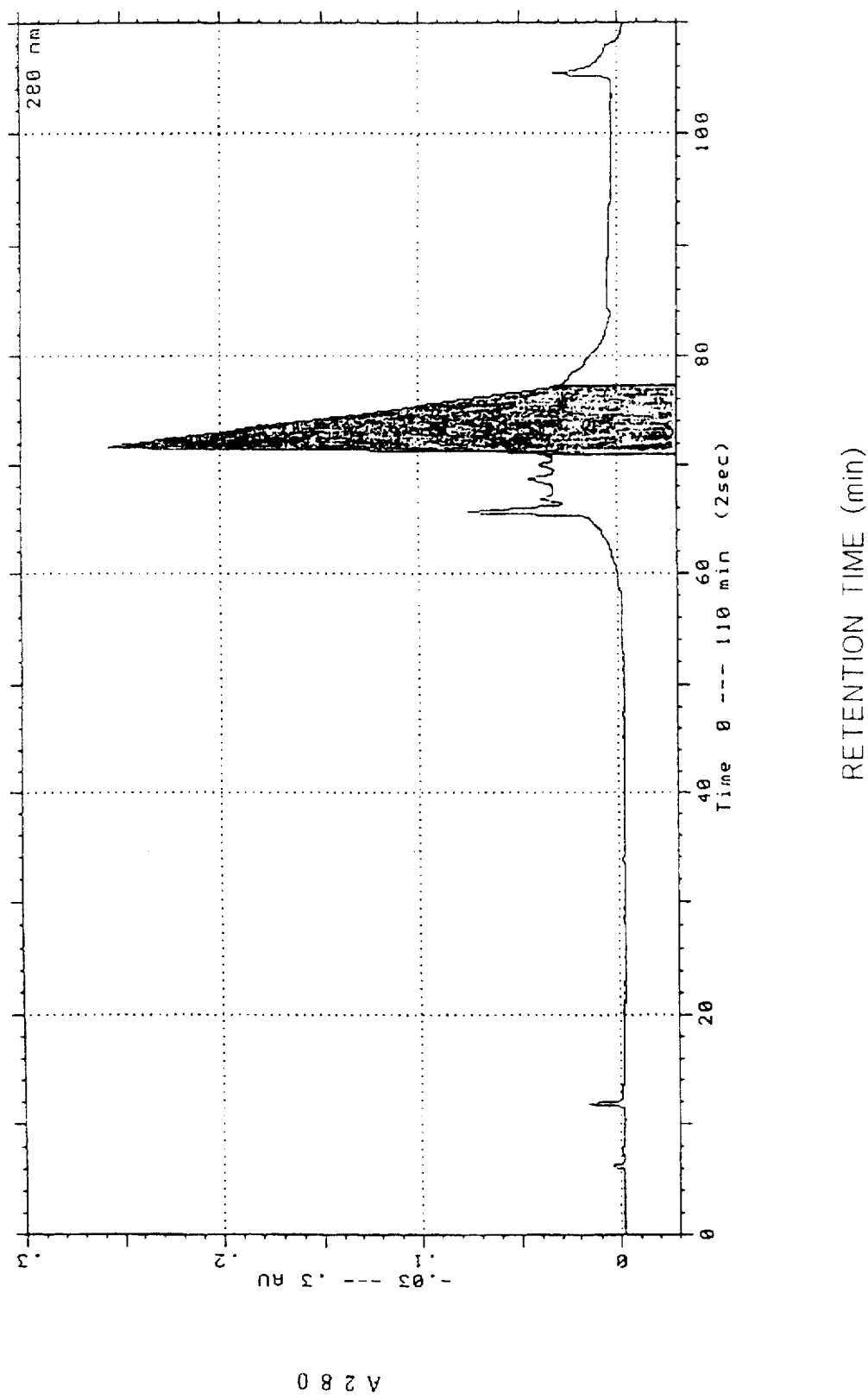
FIG. 12 is a graph showing an elution profile of C18 reversed phase HPLC of the human-derived tumor cell growth inhibitor which is the subject of the present invention.

As the result, the activity was focused on a single peak, see FIG. 12.

Experiment 2

(1) Tumor cell growth inhibitory activity of hTG-700

Tumor cells from HeLa (human uterus cancer), HCT-15 (human colon tumor), T-13 (human renal tumor) and T-28

(human renal tumor) cells were inoculated on each well of a 48 well plate in an amount of 5×10³/150 µl of 10% calf fetal serum-supplemented DF culture broth (Dulbecco's modified MEM:HamF-12=1:1). After incubation for 24 hours, the medium was removed and 200 µl of 0.1% BAS-supplemented DF culture broth containing hTG-700, which had been obtained in Example 3, 5 above, was added to the cells followed by incubation for 6 days. The culture broth was then removed. After washing with PBS(−) (0.2 g KCl, 0.2 g KH$_2$PO$_4$, 8 g NaCl, 1.15 g Na$_2$HPO$_4$, per litter), the pellet was stripped out with 0.25% trypsin and the cell count was counted with Coulter Counter (Coulter). The cell growth inhibitory activity was determined according to the following equation:

$$(\%) \text{ of Control} = \frac{\text{Cell count in the group treated with hTG-700}}{\text{Cell count in the intact group}} \times 100$$

Figure 13:
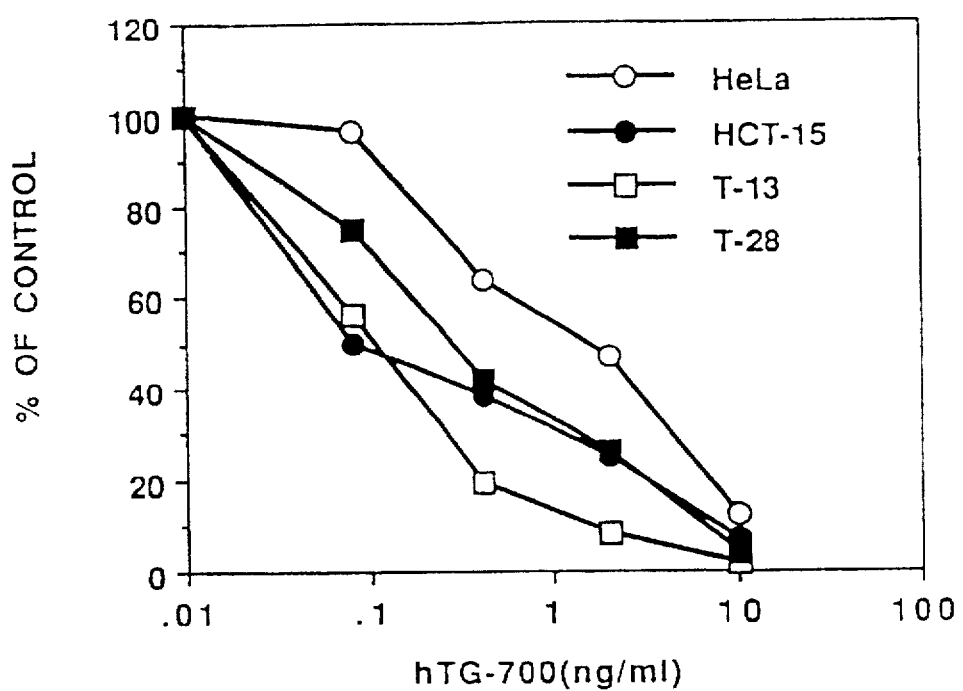
FIG. 13 is a graph showing a growth inhibitory activity of the human-derived tumor cell growth inhibitor on human tumor cells.

As is appreciated from FIG. 13, the cell growth inhibitory activity of hTG-700 was observed with respect to some of human tumor cells.

(2) Detection of hTG-700 by mouse G-700 antibody

Figure 14:
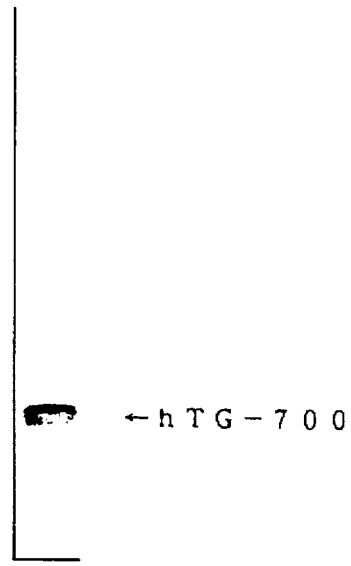
FIG. 14 is a photograph showing the results of Western blotting of the human-derived tumor cell growth inhibitor.

After 20% SDS-PAGE was performed on hTG-700 obtained in Example 3, 5 above, hTG-700 was transferred onto a nitrocellulose filter. After shaking at room temperature for an hour with 2% bovine serum albumin (BSA)-supplemented TBS solution (150 mnM NaCl, 20 mM pH 8.0), the filter was immersed in 0.1% BSA-Tris-HCl, supplemented TBS solution and allowed to stand at 4° C. overnight followed by blocking. The reaction was sequentially carried out using anti-mouse TG-700 antibody and donkey anti-rabbit IgGF (ab')$_2$ as primary and secondary antibodies, respectively. Washing between the reactions was carried out with TBS solution containing 2% Tween 20 and 10% Block Ace (Dainippon Pharmaceutical Co., Ltd.). Using ECL System (Amersham Inc.), hTG-700 was detected. Human type TG-700 was detected by the antibody to mouse TG-700 at the position of the expected molecular weight, see FIG. 14. Industrial Applicability The present invention provides novel hTG-700. This hTG-700 is expected to be effective for the treatment of leukemia, renal cancer and uterocervical cancer. The present invention further provides the DNA fragment encoding hTG-700. Utilizing the DNA fragment, hTG-700 can be produced by recombinant DNA technique. According to the present invention, hTG-700 can be expressed in *Bacillus brevis*, using the promoter and the DNA fragment encoding signal peptide as a regulator gene, originating from *Bacillus brevis*, whereby hTG-700 can be secreted out of the cell in such a form that the active steric structure is maintained. Therefore, the present invention provides hTG-700 which is expected as a new drug also provides an industrially advantageous method for producing hTG-700.

We claim:

1. An isolated human-derived tumor cell growth inhibitor consisting of the amino acid sequence shown by formula (1) (Seq. I.D. No. 1):

Val—Ser—Ile—Thr—Lys—Cys—Ser—Ser—
Asp—Met—Asn—gly—Tyr—Cys—Leu—His—
Gly—Gln—Cys—Ile—Tyr—Leu—Val—Asp—
Met—Ser—Gln—Asn—Tyr—Cys—Arg—Cys—
Glu—Val—Gly—Tyr—Thr—Gly—Val—Arg—
Cys—Glu—His—Phe—Phe—Leu.(1)

2. An isolated DNA fragment encoding a human tumor cell growth inhibitor according to a claim 1.

3. An isolated DNA fragment according to claim 2, which consists of the nucleotide sequence shown by formula (2) (Seq. I.D. No. 2):

```
                              27                                                    (2)
GTG TCA ATA ACA AAG TGT AGC TCT GAC ATG AAT GGC TAT TGT TTG CAT GGA CAG
                              81                                            108
TGC ATC TAT CTG GTG GAC ATG AGT CAA AAC TAC TGC AGG TGT GAA GTG GGT TAT
                             135
ACT GGT GTC CGA TGT GAA CAC TTC TTT TTA.
```

4. A DNA sequence comprising a promoter originating from *Bacillus brevis*, a DNA fragment encoding a signal peptide originating from *Bacillus brevis* and a DNA fragment according to claims 3.

5. An expression plasmid comprising a DNA sequence according to claim 4.

6. *Bacillus brevis* transformed by an expression plasmid according to claim 5.

7. A method for producing a human-derived tumor cell growth inhibitor by genetic engineering which comprises culturing *Bacillus brevis* of claim 6 under conditions whereby said human-derived tumor cell growth inhibitor is expressed and secreted extra cellularly, and then recovering said human-derived tumor cell growth inhibitor from the culture broth.

* * * * *

UNITED STATES PATENT AND TRADEMARK OFFICE
CERTIFICATE OF CORRECTION

PATENT NO. : 5,783,417            Page 1 of 3
DATED : July 21, 1998
INVENTOR(S) : KOMURASAKI et al It is certified that error appears in the above-indentified patent and that said Letters Patent is hereby corrected as shown below:

On the title page, item [56], Under the heading "U.S. References Cited", "U.S. 4,524,145 6/1985" should read --U.S. 4,524,145 7/1985--.

Col. 1, line 4, delete "PCT/JP94/100895" and insert --371 of PCT/JP94/00895--.

Col. 3, line 24, delete "PBR" and insert --pBR--;
       delete lines 34 & 35; and
       line 61, "CDNA" should read --cDNA--.

Col. 4, line 57, "[a-$^{32}$p]" should read --[a-$^{32}$P]--.

Col. 5, line 6, "[a-$^{32}$p]" should read --[a-$^{32}$P]--; and
       line 7, "MRNA" should read --mRNA--.

Col. 9, line 47, "CNDA" should read --cDNA--.

Col. 10, line 1, "F" should read --DF--;
       line 10, "MRNA" should read --mRNA--;
       line 30, "[$\alpha$-32p]" should read --[$\alpha$-$^{32}$P]--; and

UNITED STATES PATENT AND TRADEMARK OFFICE
CERTIFICATE OF CORRECTION

PATENT NO. : 5,783,417
DATED : July 21, 1998
INVENTOR(S) : KOMURASAKI et al

It is certified that error appears in the above-indentified patent and that said Letters Patent is hereby corrected as shown below:

line 33, "CDNA" should read --cDNA--.

Col. 12, line 55, "oligo-nucleotides" should read --oligonucleotides--;
    line 60, "Al" should read --$\mu$l-- and "Xgt10" should read --$\lambda$gt10--; and
    line 66, "22,10" should read --22, 10--.

Col. 13, line 3, begin a new paragraph with "Gene";
    line 18, "gl" should read --$\mu$l--;
    line 20, "niM" should read --mM--;
    line 34, "$\mu$of" should read --$\mu$l--;
    line 36, "$\mu$of" should read --$\mu$l--; and
    line 39, "$\mu$of" should read --$\mu$l--.

Col. 14, line 43, "$\mu$g/pl" should read --$\mu$g/$\mu$l--; and
    line 54, "PBB230" insert --pBB230--.

Col.15, line 6, "pg" should read --$\mu$g--;
    line 64, "C4" should read --$C_4$--.

UNITED STATES PATENT AND TRADEMARK OFFICE
CERTIFICATE OF CORRECTION

PATENT NO. : 5,783,417
DATED : July 21, 1998
INVENTOR(S) : KOMURASAKI et al

It is certified that error appears in the above-indentified patent and that said Letters Patent is hereby corrected as shown below:

Col. 17, line 30, "mnM" should read --mM-- and before "pH" insert --Tris-HCl,--.

Col. 18, line 1, delete "Tris-HCl".

Col. 31, line 18, "claims" should read --claim--.

Signed and Sealed this

Eighth Day of June, 1999

Q. TODD DICKINSON

*Attest:*

*Attesting Officer*  *Acting Commissioner of Patents and Trademarks*

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Val  Ser  Ile  Thr  Lys  Cys  Ser  Ser  Asp  Met  Asn  Gly  Tyr  Cys  Leu  His
 1              5                          10                         15

Gly  Gln  Cys  Ile  Tyr  Leu  Val  Asp  Met  Ser  Gln  Asn  Tyr  Cys  Arg  Cys
              20                         25                         30

Glu  Val  Gly  Tyr  Thr  Gly  Val  Arg  Cys  Glu  His  Phe  Phe  Leu
              35                         40                    45
```

( 2 ) INFORMATION FOR SEQ ID NO:2:

( i ) SEQUENCE CHARACTERISTICS:
        ( A ) LENGTH: 138 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
GTGTCAATAA CAAAGTGTAG CTCTGACATG AATGGCTATT GTTTGCATGG ACAGTGCATC      60

TATCTGGTGG ACATGAGTCA AAACTACTGC AGGTGTGAAG TGGGTTATAC TGGTGTCCGA     120

TGTGAACACT TCTTTTA                                                    138
```

(2) INFORMATION FOR SEQ ID NO:3:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
AGTGCACTCG CACTTACTGT TGCTCCCATG GCTTTCGCTG CAG                        43
```

(2) INFORMATION FOR SEQ ID NO:4:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
GATCCTGCAG CGAAAGCCAT GGGAGCAACA GTAAGTGCGA GTGCACT                    47
```

(2) INFORMATION FOR SEQ ID NO:5:

(i) SEQUENCE CHARACTERISTICS:
        (A) LENGTH: 138 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..138

(xi) SEQUENCE DESCRIPTION: SEQ ID NO:5:

```
GTG CAG ATT ACA AAG TGT AGT TCT GAC ATG GAC GGC TAC TGC TTG CAT        48
Val Gln Ile Thr Lys Cys Ser Ser Asp Met Asp Gly Tyr Cys Leu His
1               5                   10                  15

GGC CAG TGC ATC TAC CTG GTG GAC ATG AGA GAG AAA TTC TGC AGA TGT        96
Gly Gln Cys Ile Tyr Leu Val Asp Met Arg Glu Lys Phe Cys Arg Cys
                20                  25                  30

GAA GTG GGC TAC ACT GGT CTG CGA TGT GAG CAC TTC TTT CTA               138
Glu Val Gly Tyr Thr Gly Leu Arg Cys Glu His Phe Phe Leu
                35                  40                  45
```

(2) INFORMATION FOR SEQ ID NO:6:

(i) SEQUENCE CHARACTERISTICS:
        (A) LENGTH: 46 amino acids
        (B) TYPE: amino acid
        (D) TOPOLOGY: linear (ii) MOLECULE TYPE: protein (xi) SEQUENCE DESCRIPTION: SEQ ID NO:6:

```
Val Gln Ile Thr Lys Cys Ser Ser Asp Met Asp Gly Tyr Cys Leu His
1               5                   10                  15
```

```
Gly Gln Cys Ile Tyr Leu Val Asp Met Arg Glu Lys Phe Cys Arg Cys
             20                  25                  30
Glu Val Gly Tyr Thr Gly Leu Arg Cys Glu His Phe Phe Leu
         35                  40              45
```

(2) INFORMATION FOR SEQ ID NO:7:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
CAGTTCAGAC AGAAGACAAT CCACGTGTGG CTCAAGTGTC AATAACAAAG TGTAGCTCTG      60
ACATGAATGG CTATTGTTTG CATGGACAGT GCATCTATCT GGTGGACATG AGTCAAAACT    120
ACTGCAGGT                                                            129
```

(2) INFORMATION FOR SEQ ID NO:8:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
TAGTTCAGAT GGAAGACGAT CCCCGTGTGG CTCAAGTGCA GATTACAAAG TGTAGTTCTG      60
ACATGGACGG CTACTGCTTG CATGGCCAGT GCATCTACCT GGTGGACATG AGAGAGAAAT    120
TCTGCAGAT                                                            129
```

(2) INFORMATION FOR SEQ ID NO:9:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..120

(xi) SEQUENCE DESCRIPTION: SEQ ID NO:9:

```
CAG ACA GAA GAC AAT CCA CGT GTG GCT CAA GTG TCA ATA ACA AAG TGT       48
Gln Thr Glu Asp Asn Pro Arg Val Ala Gln Val Ser Ile Thr Lys Cys
 1               5                  10                  15

AGC TCT GAC ATG AAT GGC TAT TGT TTG CAT GGA CAG TGC ATC TAT CTG       96
Ser Ser Asp Met Asn Gly Tyr Cys Leu His Gly Gln Cys Ile Tyr Leu
             20                  25                  30

GTG GAC ATG AGT CAA AAC TAC TGC                                      120
Val Asp Met Ser Gln Asn Tyr Cys
             35                  40
```

(2) INFORMATION FOR SEQ ID NO:10:

(i) SEQUENCE CHARACTERISTICS:
        (A) LENGTH: 40 amino acids
        (B) TYPE: amino acid ( D ) TOPOLOGY: linear ( i i ) MOLECULE TYPE: protein ( x i ) SEQUENCE DESCRIPTION: SEQ ID NO:10:

| Gln | Thr | Glu | Asp | Asn | Pro | Arg | Val | Ala | Gln | Val | Ser | Ile | Thr | Lys | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Ser | Asp | Met | Asn | Gly | Tyr | Cys | Leu | His | Gly | Gln | Cys | Ile | Tyr | Leu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Val | Asp | Met | Ser | Gln | Asn | Tyr | Cys |
|-----|-----|-----|-----|-----|-----|-----|-----|
|     |     | 35  |     |     |     |     | 40  |

( 2 ) INFORMATION FOR SEQ ID NO:11:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..120

( x i ) SEQUENCE DESCRIPTION: SEQ ID NO:11:

| CAG | ATG | GAA | GAC | GAT | CCC | CGT | GTG | GCT | CAA | GTG | CAG | ATT | ACA | AAG | TGT | 48 |
|-----|-----|-----|-----|-----|-----|-----|-----|-----|-----|-----|-----|-----|-----|-----|-----|----|
| Gln | Met | Glu | Asp | Asp | Pro | Arg | Val | Ala | Gln | Val | Gln | Ile | Thr | Lys | Cys |    |
| 1   |     |     |     | 5   |     |     |     |     | 10  |     |     |     |     | 15  |     |    |

| AGT | TCT | GAC | ATG | GAC | GGC | TAC | TGC | TTG | CAT | GGC | CAG | TGC | ATC | TAC | CTG | 96 |
|-----|-----|-----|-----|-----|-----|-----|-----|-----|-----|-----|-----|-----|-----|-----|-----|----|
| Ser | Ser | Asp | Met | Asp | Gly | Tyr | Cys | Leu | His | Gly | Gln | Cys | Ile | Tyr | Leu |    |
|     |     |     | 20  |     |     |     |     | 25  |     |     |     |     | 30  |     |     |    |

| GTG | GAC | ATG | AGA | GAG | AAA | TTC | TGC | 120 |
|-----|-----|-----|-----|-----|-----|-----|-----|-----|
| Val | Asp | Met | Arg | Glu | Lys | Phe | Cys |     |
|     |     | 35  |     |     |     |     | 40  |     |

( 2 ) INFORMATION FOR SEQ ID NO:12:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Gln | Met | Glu | Asp | Asp | Pro | Arg | Val | Ala | Gln | Val | Gln | Ile | Thr | Lys | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Ser | Asp | Met | Asp | Gly | Tyr | Cys | Leu | His | Gly | Gln | Cys | Ile | Tyr | Leu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Val | Asp | Met | Arg | Glu | Lys | Phe | Cys |
|-----|-----|-----|-----|-----|-----|-----|-----|
|     |     | 35  |     |     |     |     | 40  |

( 2 ) INFORMATION FOR SEQ ID NO:13:

( i ) SEQUENCE CHARACTERISTICS:
        ( A ) LENGTH: 433 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..368

( x i ) SEQUENCE DESCRIPTION: SEQ ID NO:13:

| | | | | | | | | | | | | | | | | |
|---|---|---|---|---|---|---|---|---|---|---|---|---|---|---|---|---|
| TC | ACA | GCT | TTA | GTT | CAG | ACA | GAA | GAC | AAT | CCA | CGT | GTG | GCT | CAA | GTG | 47 |
| | Thr | Ala | Leu | Val | Gln | Thr | Glu | Asp | Asn | Pro | Arg | Val | Ala | Gln | Val | |
| | 1 | | | 5 | | | | | 10 | | | | | 15 | | |
| TCA | ATA | ACA | AAG | TGT | AGC | TCT | GAC | ATG | AAT | GGC | TAT | TGT | TTG | CAT | GGA | 95 |
| Ser | Ile | Thr | Lys | Cys | Ser | Ser | Asp | Met | Asn | Gly | Tyr | Cys | Leu | His | Gly | |
| | | | 20 | | | | | 25 | | | | | 30 | | | |
| CAG | TGC | ATC | TAT | CTG | GTG | GAC | ATG | AGT | CAA | AAC | TAC | TGC | AGG | TGT | GAA | 143 |
| Gln | Cys | Ile | Tyr | Leu | Val | Asp | Met | Ser | Gln | Asn | Tyr | Cys | Arg | Cys | Glu | |
| | | | 35 | | | | 40 | | | | | 45 | | | | |
| GTG | GGT | TAT | ACT | GGT | GTC | CGA | TGT | GAA | CAC | TTC | TTT | TTA | ACC | GTC | CAC | 191 |
| Val | Gly | Tyr | Thr | Gly | Val | Arg | Cys | Glu | His | Phe | Phe | Leu | Thr | Val | His | |
| | | 50 | | | | 55 | | | | | 60 | | | | | |
| CAA | CCT | TTA | AGC | AAA | GAG | TAT | GTG | GCT | TTG | ACC | GTG | ATT | CTT | ATT | ATT | 239 |
| Gln | Pro | Leu | Ser | Lys | Glu | Tyr | Val | Ala | Leu | Thr | Val | Ile | Leu | Ile | Ile | |
| | 65 | | | | 70 | | | | | 75 | | | | | | |
| TTG | TTT | CTT | ATC | ACA | GTC | GTC | GGT | TCC | ACA | TAT | TAT | TTC | TGC | AGA | TGG | 287 |
| Leu | Phe | Leu | Ile | Thr | Val | Val | Gly | Ser | Thr | Tyr | Tyr | Phe | Cys | Arg | Trp | |
| 80 | | | | | 85 | | | | 90 | | | | | 95 | | |
| TAC | AGA | AAT | CGA | AAA | AGT | AAA | GAA | CCA | AAG | AAG | GAA | TAT | GAG | AGA | GTT | 335 |
| Tyr | Arg | Asn | Arg | Lys | Ser | Lys | Glu | Pro | Lys | Lys | Glu | Tyr | Glu | Arg | Val | |
| | | | 100 | | | | | 105 | | | | | 110 | | | |
| ACC | TCA | GGG | GAT | CCA | GAG | TTG | CCG | CAA | GTC | TGAATGGCGC | | CATCAAACTT | | | | 385 |
| Thr | Ser | Gly | Asp | Pro | Glu | Leu | Pro | Gln | Val | | | | | | | |
| | | | 115 | | | | | 120 | | | | | | | | |

ATGGGCCAGG GATAACAGTG TGCCTGGTTA ATATTAATAT TCCATTTT 433

( 2 ) INFORMATION FOR SEQ ID NO:14:

( i ) SEQUENCE CHARACTERISTICS:
        ( A ) LENGTH: 121 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

Thr Ala Leu Val Gln Thr Glu Asp Asn Pro Arg Val Ala Gln Val Ser
1               5                   10                  15

Ile Thr Lys Cys Ser Ser Asp Met Asn Gly Tyr Cys Leu His Gly Gln
                20                  25                  30

Cys Ile Tyr Leu Val Asp Met Ser Gln Asn Tyr Cys Arg Cys Glu Val
            35                  40                  45

Gly Tyr Thr Gly Val Arg Cys Glu His Phe Phe Leu Thr Val His Gln
        50                  55                  60

Pro Leu Ser Lys Glu Tyr Val Ala Leu Thr Val Ile Leu Ile Ile Leu
65                  70                  75                  80

Phe Leu Ile Thr Val Val Gly Ser Thr Tyr Tyr Phe Cys Arg Trp Tyr
                85                  90                  95

Arg Asn Arg Lys Ser Lys Glu Pro Lys Lys Glu Tyr Glu Arg Val Thr
            100                 105                 110

Ser Gly Asp Pro Glu Leu Pro Gln Val
        115                 120

( 2 ) INFORMATION FOR SEQ ID NO:15:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear (i i) MOLECULE TYPE: cDNA (x i) SEQUENCE DESCRIPTION: SEQ ID NO:15:

| Val | Gln | Ile | Thr | Lys | Cys | Ser | Ser | Asp | Met | Asp | Gly | Tyr | Cys | Leu | His |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Gln | Cys | Ile | Tyr | Leu | Val | Asp | Met | Arg | Glu | Lys | Phe | Cys | Arg | Cys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Glu | Val | Gly | Tyr | Thr | Gly | Leu | Arg | Cys | Glu | His | Phe | Phe | Leu |
|-----|-----|-----|-----|-----|-----|-----|-----|-----|-----|-----|-----|-----|-----|
|     |     | 35  |     |     |     |     | 40  |     |     |     |     | 45  |     |

(2) INFORMATION FOR SEQ ID NO:16:

(i) SEQUENCE CHARACTERISTICS:
        (A) LENGTH: 46 amino acids
        (B) TYPE: amino acid
        (C) STRANDEDNESS: single
        (D) TOPOLOGY: linear (i i) MOLECULE TYPE: cDNA (x i) SEQUENCE DESCRIPTION: SEQ ID NO:16:

| Val | Ser | Ile | Thr | Lys | Cys | Ser | Ser | Asp | Met | Asn | Gly | Tyr | Cys | Leu | His |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Gln | Cys | Ile | Tyr | Leu | Val | Asp | Met | Ser | Gln | Asn | Tyr | Cys | Arg | Cys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Glu | Val | Gly | Tyr | Thr | Gly | Val | Arg | Cys | Glu | His | Phe | Phe | Leu |
|-----|-----|-----|-----|-----|-----|-----|-----|-----|-----|-----|-----|-----|-----|
|     |     | 35  |     |     |     |     | 40  |     |     |     |     | 45  |     |

(2) INFORMATION FOR SEQ ID NO:17:

(i) SEQUENCE CHARACTERISTICS:
        (A) LENGTH: 138 base pairs
        (B) TYPE: nucleic acid
        (C) STRANDEDNESS: single
        (D) TOPOLOGY: linear (i i) MOLECULE TYPE: cDNA (i x) FEATURE:
        (A) NAME/KEY: CDS
        (B) LOCATION: 1..138

(x i) SEQUENCE DESCRIPTION: SEQ ID NO:17:

| GTG | TCA | ATA | ACA | AAG | TGT | AGC | TCT | GAC | ATG | AAT | GGC | TAT | TGT | TTG | CAT | 48 |
|-----|-----|-----|-----|-----|-----|-----|-----|-----|-----|-----|-----|-----|-----|-----|-----|-----|
| Val | Ser | Ile | Thr | Lys | Cys | Ser | Ser | Asp | Met | Asn | Gly | Tyr | Cys | Leu | His | |
| 1   |     |     |     | 5   |     |     |     |     | 10  |     |     |     |     | 15  |     | |

| GGA | CAG | TGC | ATC | TAT | CTG | GTG | GAC | ATG | AGT | CAA | AAC | TAC | TGC | AGG | TGT | 96 |
|-----|-----|-----|-----|-----|-----|-----|-----|-----|-----|-----|-----|-----|-----|-----|-----|-----|
| Gly | Gln | Cys | Ile | Tyr | Leu | Val | Asp | Met | Ser | Gln | Asn | Tyr | Cys | Arg | Cys | |
|     |     |     | 20  |     |     |     |     | 25  |     |     |     |     | 30  |     |     | |

| GAA | GTG | GGT | TAT | ACT | GGT | GTC | CGA | TGT | GAA | CAC | TTC | TTT | TTA | 138 |
|-----|-----|-----|-----|-----|-----|-----|-----|-----|-----|-----|-----|-----|-----|-----|
| Glu | Val | Gly | Tyr | Thr | Gly | Val | Arg | Cys | Glu | His | Phe | Phe | Leu | |
|     |     | 35  |     |     |     |     | 40  |     |     |     |     | 45  |     | |

(2) INFORMATION FOR SEQ ID NO:18:

(i) SEQUENCE CHARACTERISTICS:
        (A) LENGTH: 46 amino acids
        (B) TYPE: amino acid
        (D) TOPOLOGY: linear (i i) MOLECULE TYPE: protein (x i) SEQUENCE DESCRIPTION: SEQ ID NO:18:

| Val | Ser | Ile | Thr | Lys | Cys | Ser | Ser | Asp | Met | Asn | Gly | Tyr | Cys | Leu | His |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

```
Gly Gln Cys Ile Tyr Leu Val Asp Met Ser Gln Asn Tyr Cys Arg Cys
         20              25                  30

Glu Val Gly Tyr Thr Gly Val Arg Cys Glu His Phe Phe Leu
         35              40                  45
```

( 2 ) INFORMATION FOR SEQ ID NO:19:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 4..30

( x i ) SEQUENCE DESCRIPTION: SEQ ID NO:19:

```
CCC ATG GCT TTC GCT GTG TCA ATA ACA AAG                         30
    Met Ala Phe Ala Val Ser Ile Thr Lys
    1               5
```

( 2 ) INFORMATION FOR SEQ ID NO:20:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Met Ala Phe Ala Val Ser Ile Thr Lys
1               5
```

( 2 ) INFORMATION FOR SEQ ID NO:21:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

```
CAAGCTTTTA TTATAAAAAG AAGTGTTCAC A                              31
```